(12) United States Patent
Nash et al.

(10) Patent No.: US 9,193,793 B2
(45) Date of Patent: Nov. 24, 2015

(54) ANTIBODIES AGAINST G-CSFR AND USES THEREOF

(75) Inventors: Andrew Donald Nash, Parkville (AU); Arna Elizabeth Andrews, Parkville (AU); Manuel Baca, Gaithersburg, MD (US); Kirsten Mae Edwards, Parkville (AU); Matthew Philip Hardy, Parkville (AU); Con Panousis, Parkville (AU); Felicity Meredith Dunlop, Bentleigh (AU)

(73) Assignee: CSL LIMITED, Parkville, Victoria (AU)

( * ) Notice: Subject to any disclaimer, the term of this patent is extended or adjusted under 35 U.S.C. 154(b) by 191 days.

(21) Appl. No.: 13/495,539

(22) Filed: Jun. 13, 2012

(65) Prior Publication Data

US 2012/0321630 A1 Dec. 20, 2012

Related U.S. Application Data

(60) Provisional application No. 61/496,351, filed on Jun. 13, 2011.

(51) Int. Cl.
| | |
|---|---|
| *A61K 39/395* | (2006.01) |
| *C07K 16/00* | (2006.01) |
| *C12P 21/08* | (2006.01) |
| *C07K 16/28* | (2006.01) |

(52) U.S. Cl.
CPC ......... *C07K 16/2866* (2013.01); *C07K 2317/21* (2013.01); *C07K 2317/33* (2013.01); *C07K 2317/34* (2013.01); *C07K 2317/55* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,422,248 A | * | 6/1995 | Smith et al. ................... 435/69.1 |
| 2010/0004167 A1 | * | 1/2010 | Yorke-Smith et al. ........... 514/12 |
| 2011/0110934 A1 | | 5/2011 | Wicks et al. |

FOREIGN PATENT DOCUMENTS

| EP | 1 167 390 A1 | 2/2002 |
| WO | 95/21867 A1 | 8/1995 |
| WO | 2008/003763 A1 | 1/2008 |
| WO | WO2008017126 A1 | 2/2008 |
| WO | WO2011/032204 A1 | 3/2011 |

OTHER PUBLICATIONS

Layton, J.E. et al., "Neutralising Antibodies to the Granulocyte Colony-stimulating Factor Receptor Recognise both the Immunoglobulin-like Domain and the Cytokine Receptor Homologous Domain" Growth Factors (Jan. 1997) pp. 117-130, vol. 14, No. 2-3.
Layton, Judith E., et al., "Neutralising Antibodies to the Granulocyte Colony-stimulating Factor Receptor Recognise both the Immunoglobulin- like Domain and the Cytokine Receptor Homologous Domain"; Growth Factors, 1997, vol. 14, pp. 117-130.
deBruin, Cortney, et al., "Most purported antibodies to the human granulocyte colony-stimulating factor receptor are not specific"; Experimental Hemotology, 38; pp. 1022-1035, 2010.
Elsässer, Annika, et al., The fusion protein AML1-ETO in actue myeloid leukemia with translocation t(8;21) induces c-jun protein expression via the proximal AP-1 site of the c-jun promoter in an indirect, JNK- dependent manner:; Oncogene (2003) 22, pp. 5646-5657.
8. Written Opinion of the International Searching Authority corresponding to PCT/AU2012/000675, dated Nov. 1, 2012.
Layton, J. E. et al., "Identification Of A Ligand-Binding Site On The Granulocyte Colony-Stimulating Factor Receptor By Molecular Modeling And Mutagenesis" Journal Of Biological Chemistry (Nov. 1997) pp. 29735-29741, vol. 272, No. 47.
Layton, J.E. et al., "The Interaction Of G-Csf With Its Receptor" Frontiers In Bioscience (Jan. 2006) pp. 3181-3189, vol. 11.
Layton, J.E. et al., "Interaction of granulocyte colony-stimulating factor (G-CSF) with its receptor: Evidence that Glu19 of G-CSF interacts with Arg288 of the receptor" Journal Of Biological Chemistry (Jun. 1999) pp. 17445-17451, vol. 274, No. 25.
Layton, J.E. et al., "Identification of Ligand-binding Site III on the Immunoglobulin-like Domain of the Granulocyte Colony-stimulating Factor Receptor" Journal Of Biological Chemistry (Jul. 2001) pp. 36779-36787, vol. 276, No. 39.
Fukunaga, R. et al., "Three Different Messenger Rnas Encoding Human Granulocyte Colony-Stimulating Factor Receptor" Proceedings Of The National Academy Of Sciences (Jan. 1990) pp. 8702-8706, vol. 87, No. 22.
Supplementary European Search Report dated May 19, 2015 issued in European Application No. EP 12800867.9.

* cited by examiner

*Primary Examiner* — Shulamith H Shafer
(74) *Attorney, Agent, or Firm* — Scully, Scott, Murphy & Presser, P.C.

(57) ABSTRACT

The present disclosure provides proteins comprising antigen binding domains of antibodies that bind to human granulocyte-colony stimulating factor receptor.

21 Claims, 4 Drawing Sheets

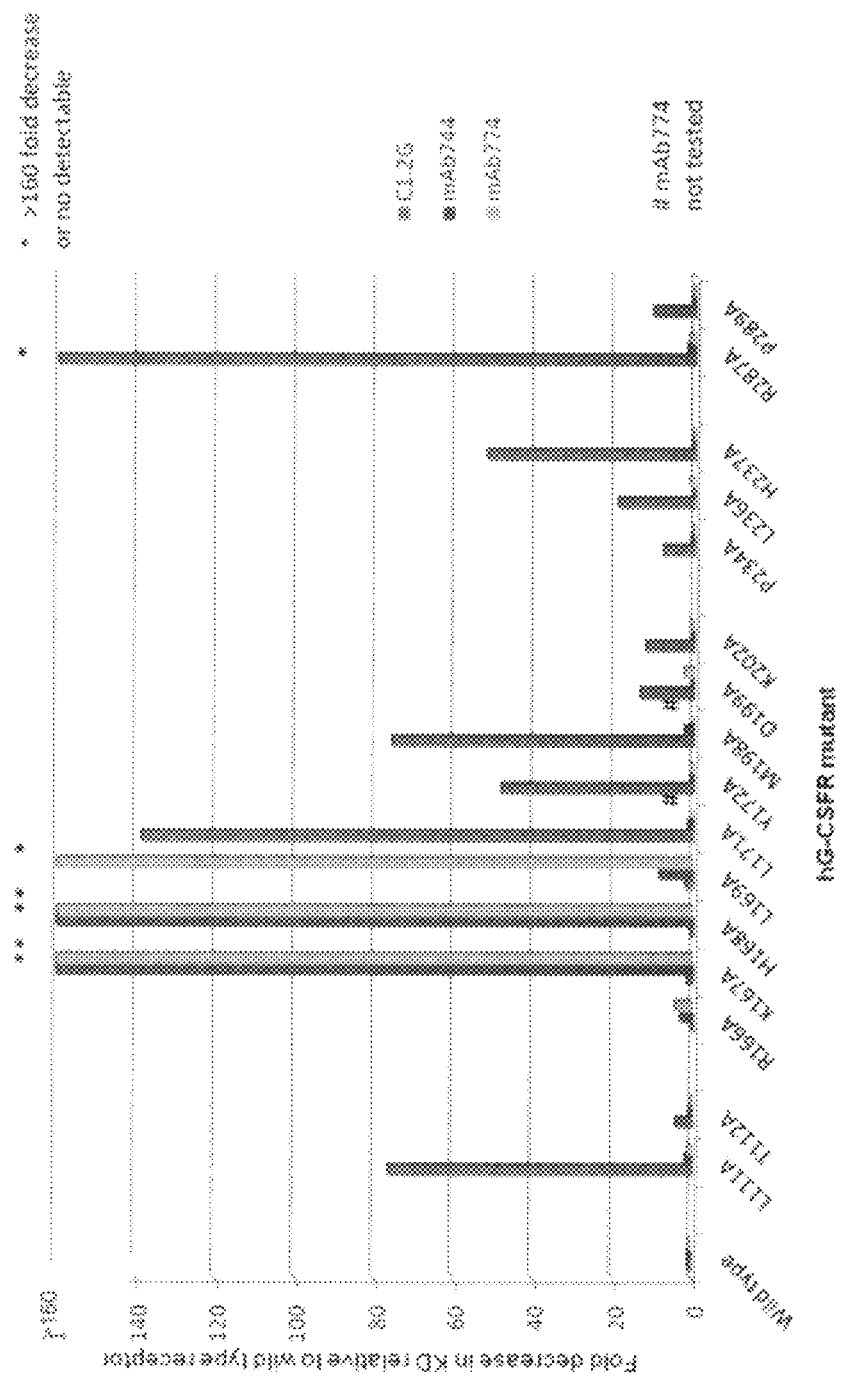

ANTIBODIES AGAINST G-CSFR AND USES THEREOF

RELATED APPLICATION

The present application claims priority from U.S. Provisional Patent Application No. 61/496,351 entitled "Antibodies against G-CSFR and uses thereof" filed on 13 Jun. 2011, the entire contents of which are hereby incorporated by referenced.

SEQUENCE LISTING

The present application is filed together with a Sequence Listing in electronic form. The entire contents of the Sequence Listing are hereby incorporated by reference.

FIELD

The present disclosure relates to antibodies that bind to granulocyte-colony stimulating factor receptor (G-CSFR) receptor and uses thereof, e.g., in therapy.

BACKGROUND

Granulocyte colony-stimulating factor (G-CSF) is a major regulator of granulocyte production. G-CSF is produced by bone marrow stromal cells, endothelial cells, macrophages, and fibroblasts, and production is induced by inflammatory stimuli. G-CSF acts through the G-CSF receptor (G-CSFR), which is expressed on early myeloid progenitors, mature neutrophils, monocytes/macrophages, T and B lymphocytes and endothelial cells. Mice deficient in G-CSF or the G-CSFR exhibit marked neutropenia, demonstrating the importance of G-CSF in steady-state granulopoiesis. However, G-CSF appears to be dispensable for emergency granulopoiesis, e.g., in response to an infection. G-CSF increases the production and release of neutrophils, mobilizes hematopoietic stem and progenitor cell, and modulates the differentiation, lifespan, and effector functions of mature neutrophils. G-CSF may also exert effects on macrophages, including expansion of monocyte/macrophage numbers, enhancement of phagocytic function, and regulation of inflammatory cytokine and chemokine production. G-CSF has also been shown to mobilize endothelial progenitor cells and induce or promote angiogenesis.

While G-CSF is used therapeutically, e.g., to treat neutropenia and/or mobilize hematopoietic stem cells, it also has negative actions in some conditions, e.g., inflammatory conditions and/or cancer. For example, administration of G-CSF exacerbates rheumatoid arthritis (RA), murine collagen-induced arthritis (CIA) and a passive transfer model of CIA in rats. G-CSF has been found in the serum and synovial fluid of RA patients. Furthermore, interleukin (IL)-1 and tumor necrosis factor α (TNFα), which are found at increased levels in patients suffering from RA, induce the production of G-CSF by human synovial fibroblasts and chondrocytes. Mice deficient in G-CSF are resistant to the induction of acute and chronic inflammatory arthritis.

G-CSF has also been shown to play a role in multiple sclerosis (MS). For example, G-CSF enhances adhesion of an auto-reactive T cell line model of MS to extracellular matrix as effectively as interferon γ and TNFα, which are known to exacerbate MS symptoms. Moreover, G-CSF deficient mice are resistant to development of experimental autoimmune encephalomyelitis (EAE).

G-CSF and G-CSFR have also been tied to cancer, with studies showing that this signaling pathway contributes to chemotherapy resistance, growth, survival, invasiveness and metastasis of various cancers. Moreover, G-CSF has been shown to induce to angiogenesis, a process important in the development of solid tumors.

It will be clear to the skilled person from the foregoing, that there is a need in the art for reagents that reduce the signaling of G-CSF through the G-CSFR. Exemplary agents will be suitable for use as therapeutics, e.g., to treat or prevent a G-CSF-mediated condition.

SUMMARY

The present inventors have produced a class of proteins comprising antibody binding sites (e.g., Fabs and antibodies) that bind to human G-CSFR (hG-CSFR) and potently neutralize G-CSF signaling, e.g., prevent formation of granulocytes from $CD34^+$ bone marrow cells and/or prevent cell proliferation in response to G-CSF and/or reduce or prevent neutrophilia induced by administration of G-CSF. A class of proteins identified by the inventors also cross-react cynomolgus monkey G-CSFR (cynoG-CSFR), which facilitates pre-clinical studies with the proteins. A class of proteins identified by the inventors bind to hG-CSFR with high affinity. A class of proteins identified by the inventors are human antibodies, which are suitable for treatment of a variety of conditions.

The present disclosure provides a protein comprising an antigen binding site of an antibody, wherein the antigen binding site binds to hG-CSFR and neutralizes G-CSF signaling, and wherein the protein inhibits growth of colony forming units—granulocytes (CFU-G) from $CD34^+$ bone marrow cells grown in the presence of G-CSF with an $IC_{50}$ of at least about 0.2 nM. For example, the $IC_{50}$ is 0.1 nM or less, for example, 0.09 nM or less, or 0.08 nM or less, or 0.07 nM or less, or 0.06 nM or less or 0.05 nM or less. In one example, the $IC_{50}$ is 0.04 nM or less. In another example, the $IC_{50}$ is 0.02 nM or less. Methods for assessing $IC_{50}$ of a protein in such an assay are described herein. For example, the $IC_{50}$ is determined in the presence of 10 ng/ml of hG-CSF.

In one example, the $IC_{50}$ is determined by culturing $CD34^+$ bone marrow cells in the presence of 10 ng/ml stem cell factor and 10 ng/ml hG-CSF. For example, the cells are grown in semi-solid cell culture medium. In one example, the CFU-G are enumerated after 14 days of culture.

The present disclosure additionally or alternatively provides a protein comprising an antigen binding site of an antibody, wherein the antigen binding site binds to both human and cynomolgus monkey G-CSFR with a similar affinity and neutralizes G-CSF signaling. Such proteins are advantageous since they facilitate pre-clinical studies in non-human mammals.

In one example, the affinity of the protein is determined using a biosensor, e.g., by surface plasmon resonance. For example, the ligand binding region or soluble hG-CSFR or soluble cynoG-CSFR or hG-CSFR-Fc or cyno-G-CSFR-Fc is immobilized and the affinity of the protein of the disclosure is determined.

The present disclosure additionally provides a provides a protein comprising an antigen binding site of an antibody, wherein the antigen binding site binds specifically to the same epitope in hG-CSFR as that bound by C1.2 (comprising a heavy chain variable region ($V_H$) comprising a sequence set forth in SEQ ID NO: 2 and a light chain variable region ($V_L$) comprising a sequence set forth in SEQ ID NO: 3) or C1.2G (comprising a $V_H$ comprising a sequence set forth in SEQ ID NO: 4 and a $V_L$ comprising a sequence set forth in SEQ ID NO: 5).

The present disclosure additionally or alternatively provides a protein comprising an antigen binding site of an antibody, wherein (i) the protein competitively inhibits binding of C1.2 (comprising a $V_H$ comprising a sequence set forth in SEQ ID NO: 2 and a $V_L$ comprising a sequence set forth in SEQ ID NO: 3) or C1.2G (comprising a $V_H$ comprising a sequence set forth in SEQ ID NO: 4 and a $V_L$ comprising a sequence set forth in SEQ ID NO: 5) to hG-CSFR; (ii) the protein neutralizes G-CSF signaling; and (iii) the level of binding of the protein to a polypeptide of SEQ ID NO: 1 in which an alanine is substituted for any one of:
  (a) the arginine at position 287 of SEQ ID NO:1;
  (b) the histidine at position 237 of SEQ ID NO:1;
  (c) the methionine at position 198 of SEQ ID NO:1;
  (d) the tyrosine at position 172 of SEQ ID NO:1;
  (e) the leucine at position 171 of SEQ ID NO:1; or
  (f) the leucine at position 111 of SEQ ID NO:1
is lower than the level of binding of the protein to a polypeptide of SEQ ID NO: 1.

The present disclosure additionally or alternatively provides a protein comprising an antigen binding site of an antibody, wherein (i) the protein competitively inhibits binding of C1.2 (comprising a $V_H$ comprising a sequence set forth in SEQ ID NO: 2 and a $V_L$ comprising a sequence set forth in SEQ ID NO: 3) or C1.2G (comprising a $V_H$ comprising a sequence set forth in SEQ ID NO: 4 and a $V_L$ comprising a sequence set forth in SEQ ID NO: 5) to hG-CSFR; (ii) the protein neutralizes G-CSF signaling; and (iii) preferentially binds to a polypeptide of SEQ ID NO: 1 relative to its ability to bind to a polypeptide of SEQ ID NO: 1 in which an alanine is substituted for any one of:
  (a) the arginine at position 287 of SEQ ID NO:1;
  (b) the histidine at position 237 of SEQ ID NO:1;
  (c) the methionine at position 198 of SEQ ID NO:1;
  (d) the tyrosine at position 172 of SEQ ID NO:1;
  (e) the leucine at position 171 of SEQ ID NO:1; or
  (f) the leucine at position 111 of SEQ ID NO:1.

The present disclosure additionally or alternatively provides a protein comprising an antigen binding site of an antibody, wherein (i) the protein binds to hG-CSFR; (ii) the protein neutralizes G-CSF signaling; and (iii) the level of binding of the protein to a polypeptide of SEQ ID NO: 1 in which an alanine is substituted for any one of:
  (a) the arginine at position 287 of SEQ ID NO:1
  (b) the histidine at position 237 of SEQ ID NO:1;
  (c) the methionine at position 198 of SEQ ID NO:1;
  (d) the tyrosine at position 172 of SEQ ID NO:1;
  (e) the leucine at position 171 of SEQ ID NO:1; or
  (f) the leucine at position 111 of SEQ ID NO:1
is lower than the level of binding of the protein to a polypeptide of SEQ ID NO: 1.

The present disclosure additionally or alternatively provides a protein comprising an antigen binding site of an antibody, wherein (i) the protein binds to hG-CSFR; (ii) the protein neutralizes G-CSF signaling; and (iii) preferentially binds to a polypeptide of SEQ ID NO: 1 relative to its ability to bind to a polypeptide of SEQ ID NO: 1 in which an alanine is substituted for any one of:
  (a) the arginine at position 287 of SEQ ID NO:1
  (b) the histidine at position 237 of SEQ ID NO:1;
  (c) the methionine at position 198 of SEQ ID NO:1;
  (d) the tyrosine at position 172 of SEQ ID NO:1;
  (e) the leucine at position 171 of SEQ ID NO:1; or
  (f) the leucine at position 111 of SEQ ID NO:1.

In one example, the level of binding of the protein to the polypeptide comprising the alanine substitution is reduced by at least about 10 fold or 20 fold or 50 fold or 100 fold or 150 fold or 200 fold compared to the binding of the protein to the polypeptide of SEQ ID NO: 1. Preferably, the level of binding of the protein to the polypeptide comprising the alanine substitution is reduced by at least about 50 fold. Preferably, the level of binding of the protein to the polypeptide comprising the alanine substitution is reduced by at least about 60 fold.

In one example, the antigen binding site of the protein does not detectably bind to a polypeptide of SEQ ID NO: 1 in which an alanine is substituted for the arginine at position 287 of SEQ ID NO: 1.

In one example, the level of binding is assessed using a biosensor, e.g., by surface plasmon resonance. For example, the protein is immobilized and the level of binding to a polypeptide of SEQ ID NO: 1 or to a form of the polypeptide comprising an alanine substitution is determined Additional forms of a polypeptide comprising the amino acids of SEQ ID NO: 1 with or without other substitutions bound or not significantly bound or not detectably bound by a protein of the present disclosure are described herein and are to be taken to apply mutatis mutandis to the present examples of the disclosure.

In one example, the antigen binding site cross-reacts with:
(i) a polypeptide of SEQ ID NO: 1 in which an alanine is substituted for the lysine at position 167 of SEQ ID NO: 1; and/or
(ii) a polypeptide of SEQ ID NO: 1 in which an alanine is substituted for the histidine at position 168 of SEQ ID NO: 1.

In one example, the antigen binding site additionally cross-reacts with a polypeptide of SEQ ID NO: 1 in which an alanine is substituted for the leucine at position 169 of SEQ ID NO: 1

In one example, the protein competitively inhibits the binding of C1.2 (comprising a $V_H$ comprising a sequence set forth in SEQ ID NO: 2 and a $V_L$ comprising a sequence set forth in SEQ ID NO: 3) or C1.2G (comprising a $V_H$ comprising a sequence set forth in SEQ ID NO: 4 and a $V_L$ comprising a sequence set forth in SEQ ID NO: 5) to one or more of:
(i) a polypeptide of SEQ ID NO: 1 in which an alanine is substituted for the lysine at a position 167 of SEQ ID NO: 1; and/or
(ii) a polypeptide of SEQ ID NO: 1 in which an alanine is substituted for the histidine at position 168 of SEQ ID NO: 1.

In one example, a protein described herein according to any example binds to an epitope comprising residues within one or two or three or four regions selected from 111-115, 170-176, 218-234 and/or 286-300 of SEQ ID NO: 1.

In one example, upon binding of a protein described herein according to any example to a polypeptide of SEQ ID NO: 1 and cleavage using protelolytic enzymes remains bound to one or two or three or four peptides comprising or consisting of amino acids 111-115 of SEQ ID NO: 1 or amino acids 170-176 of SEQ ID NO: 1 or amino acids 218-234 of SEQ ID NO: 1 or amino acids 286-300 of SEQ ID NO: 1.

In one example, the protein binds to a conformational epitope.

The present disclosure additionally or alternatively provides a protein that binds to hG-CSFR and neutralizes G-CSF signaling, the protein comprising at least one of:
(i) a $V_H$ comprising a complementarity determining region (CDR) 1 comprising a sequence set forth in SEQ ID NO: 6, a CDR2 comprising a sequence set forth in SEQ ID NO: 7 and a CDR3 comprising a sequence at least about 55% identity to the sequence set forth in SEQ ID NO: 8;

(ii) a $V_H$ comprising a sequence at least about 80%, such as 85% or 90% or 91% or 92% or 93% or 94% or 95% or 96% or 97% or 98% or 99% identical to a sequence set forth in SEQ ID NO: 2 and/or 4;

(iii) a $V_L$ comprising a CDR1 comprising a sequence set forth in SEQ ID NO: 9, a CDR2 comprising a sequence set forth in SEQ ID NO: 10 and a CDR3 comprising a sequence at least about 33% identity to the sequence set forth in SEQ ID NO: 11; and (iv) a $V_L$ comprising a sequence at least about 80%, such as 85% or 90% or 91% or 92% or 93% or 94% or 95% or 96% or 97% or 98% or 99% identical to a sequence set forth in SEQ ID NO: 3 and/or 5.

Such a protein can comprise any one or more of the functional activities described herein, e.g., preferential binding to a polypeptide of SEQ ID NO: 1 relative to the level of binding of a polypeptide of SEQ ID NO: 1 in which an alanine is substituted for any one of:

(a) the arginine at position 287 of SEQ ID NO:1
(b) the histidine at position 237 of SEQ ID NO:1;
(c) the methionine at position 198 of SEQ ID NO:1;
(d) the tyrosine at position 172 of SEQ ID NO:1;
(e) the leucine at position 171 of SEQ ID NO:1; or
(f) the leucine at position 111 of SEQ ID NO:1.

In one example, the percentage identity at (ii) is at least about 95%.

In one example, the percentage identity at (iv) is at least about 94%.

In one example, differences between the recited sequence and the protein are substitutions.

The skilled artisan will be capable of determining sites for mutations to a protein of the disclosure, e.g., within a framework region of a variable region containing protein. Moreover, the inventors have identified numerous sites in a $V_H$ CDR3 and a $V_L$ CDR3 that can be mutated as well as numerous mutations that maintain activity of a protein of the disclosure. For example a mutation, e.g., a substitution is within one or more (e.g., 2 or 3 or 4) of the four C-terminal residues of HCDR3 and/or one or more (e.g., 2 or 3 or 4 or 5 or 6) of the N-terminal or C-terminal residues of LCDR3. In one example, the N-terminal five amino acids of $V_H$ CDR3 are LGELG. In one example, the three N-terminal amino acids of $V_L$ CDR3 are QQS and/or the three C-terminal amino acids of $V_L$ CDR3 are PLT.

In one example, the $V_H$ comprises a CDR3 comprising a sequence LGELG$X_1X_2X_3X_4$, wherein:

$X_1$ is selected from the group consisting of tryptophan, glutamine, methionine, serine, phenylalanine, glutamic acid and histidine and/or is a neutral amino acid, such as tryptophan, glutamine or methionine, for example, the amino acid is tryptophan;

$X_2$ is an amino acid selected from the group consisting of phenylalanine, tyrosine, methionine, serine, glycine and isoleucine, for example is phenylalanine, tyrosine, methionine or serine, for example, the amino acid is phenylalanine;

$X_3$ is an amino acid selected from the group consisting of aspartic acid, methionine, glutamine, serine, leucine, valine, arginine and histidine, for example, is proline, glutamic acid, alanine, leucine, phenylalanine or tyrosine, for example, the amino acid is aspartic acid; and $X_4$ is any amino acid or an amino acid selected from the group consisting of proline, glutamic acid, alanine, leucine, phenylalanine, tyrosine, threonine, asparagine, aspartic acid, serine, glycine, arginine, and lysine, for example, the amino acid is proline.

In one example, the $V_L$ comprises a CDR3 comprising a sequence $X_1X_2X_3X_4X_5X_6X_7X_8X_9$, wherein:

$X_1$ is an amino acid selected from the group consisting of glutamine, glutamic acid, histidine, alanine and serine and/or is a hydrophilic amino acid, such as glutamine or glutamic acid, for example, the amino acid is glutamine;

$X_2$ is an amino acid selected from the group consisting of glutamine, valine, phenylalanine, asparagine and glutamic acid, for example, the amino acid is glutamine;

$X_3$ is an amino acid selected from the group consisting of serine and glycine, for example, the amino acid is serine;

$X_4$ is an amino acid selected from the group consisting of tryptophan, methionine, phenylalanine, tyrosine, isoleucine and leucine, for example, the amino acid is tryptophan or tyrosine;

$X_5$ is any amino acid or an amino acid selected from the group consisting of glutamic acid, methionine, glutamine, tryptophan, serine, valine, asparagine, glycine, alanine, arganine, histidine, tyrosine, lysine and threonine, for example, the amino acid is serine;

$X_6$ is an amino acid selected from the group consisting of tyrosine, methionine, isoleucine and threonine, for example, the amino acid is methionine, tyrosine or threonine;

$X_7$ is an amino acid selected from the group consisting of proline, alanine, histidine, glycine and lysine, for example the amino acid is proline;

$X_8$ is an amino acid selected from the group consisting of leucine, glutamine, methionine, alanine, phenylalanine, isoleucine, lysine, histidine and glycine, for example, the amino acid is leucine;

$X_9$ is any amino acid or an amino acid selected from the group consisting of threonine, phenylalanine, tyrosine, methionine, lysine, serine, histidine, proline, tryptophan, isoleucine, glutamine, glycine and valine, for example, the amino acid is threonine.

The present disclosure additionally or alternatively provides a protein (e.g., an antibody) that binds to hG-CSFR and neutralizes G-CSF signaling, the protein comprising at least one variable region of an antibody selected from the group consisting of:

(i) a $V_H$ comprising an amino acid sequence set forth in SEQ ID NO: 2;
(ii) a $V_L$ comprising an amino acid sequence set forth in SEQ ID NO: 3;
(iii) a $V_H$ comprising an amino acid sequence set forth in SEQ ID NO: 4;
(iv) a $V_L$ comprising an amino acid sequence set forth in SEQ ID NO: 5;
(v) a $V_L$ comprising an amino acid sequence set forth in SEQ ID NO: 14;
(vi) a $V_H$ comprising an amino acid sequence set forth in SEQ ID NO: 15;
(vii) a $V_L$ comprising an amino acid sequence set forth in SEQ ID NO: 16;
(viii) a $V_L$ comprising an amino acid sequence set forth in SEQ ID NO: 17;
(ix) a $V_L$ comprising an amino acid sequence set forth in SEQ ID NO: 18;
(x) a $V_L$ comprising an amino acid sequence set forth in SEQ ID NO: 19;
(xi) a $V_H$ comprising an amino acid sequence set forth in SEQ ID NO: 20;
(xii) a $V_L$ comprising an amino acid sequence set forth in SEQ ID NO: 21;
(xiii) a $V_L$ comprising an amino acid sequence set forth in SEQ ID NO: 22;

(xiv) a $V_L$ comprising an amino acid sequence set forth in SEQ ID NO: 23;
(xv) a $V_H$ comprising an amino acid sequence set forth in SEQ ID NO: 24;
(xvi) a $V_L$ comprising an amino acid sequence set forth in SEQ ID NO: 25;
(xvii) a $V_L$ comprising an amino acid sequence set forth in SEQ ID NO: 26;
(xviii) a $V_L$ comprising an amino acid sequence set forth in SEQ ID NO: 27;
(xix) a $V_H$ comprising an amino acid sequence set forth in SEQ ID NO: 28;
(xx) a $V_L$ comprising an amino acid sequence set forth in SEQ ID NO: 29;
(xxi) a $V_L$ comprising an amino acid sequence set forth in SEQ ID NO: 30;
(xxii) a $V_H$ comprising an amino acid sequence set forth in SEQ ID NO: 31;
(xxiii) a $V_L$ comprising an amino acid sequence set forth in SEQ ID NO: 32;
(xxiv) a $V_H$ comprising an amino acid sequence set forth in SEQ ID NO: 33;
(xxv) a $V_L$ comprising an amino acid sequence set forth in SEQ ID NO: 34;
(xxvi) a $V_L$ comprising an amino acid sequence set forth in SEQ ID NO: 35;
(xxvii) a $V_H$ comprising an amino acid sequence set forth in SEQ ID NO: 36;
(xxviii) a $V_L$ comprising an amino acid sequence set forth in SEQ ID NO: 37;
(xxix) a $V_H$ comprising an amino acid sequence set forth in SEQ ID NO: 38;
(xxx) a $V_L$ comprising an amino acid sequence set forth in SEQ ID NO: 39;
(xxxi) a $V_H$ comprising an amino acid sequence set forth in SEQ ID NO: 40;
(xxxii) a $V_L$ comprising an amino acid sequence set forth in SEQ ID NO: 41;
(xxxiii) a $V_H$ comprising an amino acid sequence set forth in SEQ ID NO: 42;
(xxxiv) a $V_L$ comprising an amino acid sequence set forth in SEQ ID NO: 43;
(xxxv) a $V_L$ comprising an amino acid sequence set forth in SEQ ID NO: 44;
(xxxvi) a $V_H$ comprising an amino acid sequence set forth in SEQ ID NO: 45;
(xxxvii) a $V_L$ comprising an amino acid sequence set forth in SEQ ID NO: 46;
(xxxviii) a $V_L$ comprising an amino acid sequence set forth in SEQ ID NO: 47;
(xxix) a $V_L$ comprising an amino acid sequence set forth in SEQ ID NO: 48;
(xl) a $V_H$ comprising an amino acid sequence set forth in SEQ ID NO: 49;
(xli) a $V_L$ comprising an amino acid sequence set forth in SEQ ID NO: 50;
(xlii) a $V_H$ comprising an amino acid sequence set forth in SEQ ID NO: 51;
(xliii) a $V_L$ comprising an amino acid sequence set forth in SEQ ID NO: 52;
(xliv) a $V_H$ comprising an amino acid sequence set forth in SEQ ID NO: 53;
(xlv) a $V_L$ comprising an amino acid sequence set forth in SEQ ID NO: 54;
(xlvi) a $V_H$ comprising an amino acid sequence set forth in SEQ ID NO: 55;
(xlvii) a $V_L$ comprising an amino acid sequence set forth in SEQ ID NO: 56;
(xlviii) a $V_H$ comprising an amino acid sequence set forth in SEQ ID NO: 57;
(xlix) a $V_L$ comprising an amino acid sequence set forth in SEQ ID NO: 58;
(l) a $V_H$ comprising an amino acid sequence set forth in SEQ ID NO: 59;
(li) a $V_L$ comprising an amino acid sequence set forth in SEQ ID NO: 60;
(lii) a $V_H$ comprising an amino acid sequence set forth in SEQ ID NO: 61;
(liii) a $V_L$ comprising an amino acid sequence set forth in SEQ ID NO: 62; and
(liv) a $V_L$ comprising an amino acid sequence set forth in SEQ ID NO: 63.

In one example, a protein described herein comprises at least a $V_H$ and a $V_L$, wherein the $V_H$ and $V_L$ bind to form a Fv comprising an antigen binding domain. The skilled artisan will understand that the antigen binding domain comprises the binding site of the antibody.

In one example, the $V_H$ and the $V_L$ are in a single polypeptide chain. For example, the protein is:
(i) a single chain Fv fragment (scFv);
(ii) a dimeric scFv (di-scFv); or
(iii) at least one of (i) and/or (ii) linked to a constant region of an antibody, Fc or a heavy chain constant domain ($C_H$) 2 and/or $C_H$3.

In one example, the $V_L$ and $V_H$ are in separate polypeptide chains.

For example, the protein is:
(i) a diabody;
(ii) a triabody;
(iii) a tetrabody;
(iv) a Fab;
(v) a F(ab')$_2$;
(vi) a Fv; or
(vii) one of (i) to (vi) linked to a constant region of an antibody, Fc or a heavy chain constant domain ($C_H$) 2 and/or $C_H$3.

The foregoing proteins (described in the previous two lists) can also be referred to as antigen binding domains of antibodies.

In one example, the protein is an antibody. In one example, the antibody is a naked antibody.

In one example, a protein is chimeric, de-immunized, humanized, human or primatized.

In one example, the protein or antibody is human.
(i) a $V_H$ comprising an amino acid sequence set forth in SEQ ID NO: 2 and a $V_L$ comprising an amino acid sequence set forth in SEQ ID NO: 3;
(ii) a $V_H$ comprising an amino acid sequence set forth in SEQ ID NO: 4 and a $V_L$ comprising an amino acid sequence set forth in SEQ ID NO: 5;
(iii) a $V_H$ comprising an amino acid sequence set forth in SEQ ID NO: 15 and a $V_L$ comprising an amino acid sequence set forth in SEQ ID NO: 14;
(iv) a $V_H$ comprising an amino acid sequence set forth in SEQ ID NO: 4 and a $V_L$ comprising an amino acid sequence set forth in SEQ ID NO: 16;
(v) a $V_H$ comprising an amino acid sequence set forth in SEQ ID NO: 4 and a $V_L$ comprising an amino acid sequence set forth in SEQ ID NO: 17;
(vi) a $V_H$ comprising an amino acid sequence set forth in SEQ ID NO: 4 and a $V_L$ comprising an amino acid sequence set forth in SEQ ID NO: 18;

(vii) a $V_H$ comprising an amino acid sequence set forth in SEQ ID NO: 20 and a $V_L$ comprising an amino acid sequence set forth in SEQ ID NO: 19;
(viii) a $V_H$ comprising an amino acid sequence set forth in SEQ ID NO: 4 and a $V_L$ comprising an amino acid sequence set forth in SEQ ID NO: 21;
(ix) a $V_H$ comprising an amino acid sequence set forth in SEQ ID NO: 4 and a $V_L$ comprising an amino acid sequence set forth in SEQ ID NO: 22;
(x) a $V_H$ comprising an amino acid sequence set forth in SEQ ID NO: 24 and a $V_L$ comprising an amino acid sequence set forth in SEQ ID NO: 23;
(ix) a $V_H$ comprising an amino acid sequence set forth in SEQ ID NO: 4 and a $V_L$ comprising an amino acid sequence set forth in SEQ ID NO: 25;
(x) a $V_H$ comprising an amino acid sequence set forth in SEQ ID NO: 4 and a $V_L$ comprising an amino acid sequence set forth in SEQ ID NO: 26;
(xi) a $V_H$ comprising an amino acid sequence set forth in SEQ ID NO: 28 and a $V_L$ comprising an amino acid sequence set forth in SEQ ID NO: 27;
(xii) a $V_H$ comprising an amino acid sequence set forth in SEQ ID NO: 4 and a $V_L$ comprising an amino acid sequence set forth in SEQ ID NO: 29;
(xiii) a $V_H$ comprising an amino acid sequence set forth in SEQ ID NO: 31 and a $V_L$ comprising an amino acid sequence set forth in SEQ ID NO: 30;
(xiv) a $V_H$ comprising an amino acid sequence set forth in SEQ ID NO: 33 and a $V_L$ comprising an amino acid sequence set forth in SEQ ID NO: 32;
(xv) a $V_H$ comprising an amino acid sequence set forth in SEQ ID NO: 4 and a $V_L$ comprising an amino acid sequence set forth in SEQ ID NO: 34;
(xvi) a $V_H$ comprising an amino acid sequence set forth in SEQ ID NO: 36 and a $V_L$ comprising an amino acid sequence set forth in SEQ ID NO: 35;
(xvii) a $V_H$ comprising an amino acid sequence set forth in SEQ ID NO: 38 and a $V_L$ comprising an amino acid sequence set forth in SEQ ID NO: 37;
(xviii) a $V_H$ comprising an amino acid sequence set forth in SEQ ID NO: 40 and a $V_L$ comprising an amino acid sequence set forth in SEQ ID NO: 39;
(xix) a $V_H$ comprising an amino acid sequence set forth in SEQ ID NO: 42 and a $V_L$ comprising an amino acid sequence set forth in SEQ ID NO: 41;
(xx) a $V_H$ comprising an amino acid sequence set forth in SEQ ID NO: 4 and a $V_L$ comprising an amino acid sequence set forth in SEQ ID NO: 43;
(xxi) a $V_H$ comprising an amino acid sequence set forth in SEQ ID NO: 45 and a $V_L$ comprising an amino acid sequence set forth in SEQ ID NO: 44;
(xxii) a $V_H$ comprising an amino acid sequence set forth in SEQ ID NO: 4 and a $V_L$ comprising an amino acid sequence set forth in SEQ ID NO: 46;
(xxiii) a $V_H$ comprising an amino acid sequence set forth in SEQ ID NO: 4 and a $V_L$ comprising an amino acid sequence set forth in SEQ ID NO: 47;
(xxiv) a $V_H$ comprising an amino acid sequence set forth in SEQ ID NO: 51 and a $V_L$ comprising an amino acid sequence set forth in SEQ ID NO: 48;
(xxv) a $V_H$ comprising an amino acid sequence set forth in SEQ ID NO: 51 and a $V_L$ comprising an amino acid sequence set forth in SEQ ID NO: 50;
(xxvi) a $V_H$ comprising an amino acid sequence set forth in SEQ ID NO: 53 and a $V_L$ comprising an amino acid sequence set forth in SEQ ID NO: 52;
(xxvii) a $V_H$ comprising an amino acid sequence set forth in SEQ ID NO: 4 and a $V_L$ comprising an amino acid sequence set forth in SEQ ID NO: 54;
(xxviii) a $V_H$ comprising an amino acid sequence set forth in SEQ ID NO: 55 and a $V_L$ comprising an amino acid sequence set forth in SEQ ID NO: 5;
(xxix) a $V_H$ comprising an amino acid sequence set forth in SEQ ID NO: 57 and a $V_L$ comprising an amino acid sequence set forth in SEQ ID NO: 56;
(xxx) a $V_H$ comprising an amino acid sequence set forth in SEQ ID NO: 59 and a $V_L$ comprising an amino acid sequence set forth in SEQ ID NO: 58;
(xxxi) a $V_H$ comprising an amino acid sequence set forth in SEQ ID NO: 61 and a $V_L$ comprising an amino acid sequence set forth in SEQ ID NO: 60;
(xxxii) a $V_H$ comprising an amino acid sequence set forth in SEQ ID NO: 4 and a $V_L$ comprising an amino acid sequence set forth in SEQ ID NO: 62;
(xxxiii) a $V_H$ comprising an amino acid sequence set forth in SEQ ID NO: 4 and a $V_L$ comprising an amino acid sequence set forth in SEQ ID NO: 63; and
(xxxix) a $V_H$ comprising three CDRs of a $V_H$ set forth in any one or more of (i) to (xxxiii) and a $V_L$ comprising three CDRs of a $V_L$ set forth in any one or more of (i) to (xxxiii).

Sequences of exemplary $V_H$ and $V_L$ are described in Table 3, wherein the recited $V_H$ or $V_L$ CDR3 sequence is substituted for the corresponding sequence in the $V_H$ or $V_L$ of C1.2 or C1.2G as described herein.

In one example, the present disclosure provides an antibody that binds to hG-CSFR and neutralizes G-CSF signaling, the antibody comprising:
(i) a $V_H$ comprising an amino acid sequence set forth in SEQ ID NO: 2 and a $V_L$ comprising an amino acid sequence set forth in SEQ ID NO: 3; or
(ii) a $V_H$ comprising an amino acid sequence set forth in SEQ ID NO: 4 and a $V_L$ comprising an amino acid sequence set forth in SEQ ID NO: 5.

The present disclosure additionally or alternatively provides an antibody comprising a heavy chain comprising an amino acid sequence set forth in SEQ ID NO: 64 and a light chain comprising an amino acid sequence set forth in SEQ ID NO: 65. In one example, the antibody binds to hG-CSFR and neutralizes G-CSF signaling.

The present disclosure additionally or alternatively provides an antibody comprising a heavy chain comprising an amino acid sequence set forth in SEQ ID NO: 68 and a light chain comprising an amino acid sequence set forth in SEQ ID NO: 65. In one example, the antibody binds to hG-CSFR and neutralizes G-CSF signaling.

The present disclosure additionally or alternatively provides an antibody comprising one heavy chain comprising an amino acid sequence set forth in SEQ ID NO: 64 and one heavy chain comprising an amino acid sequence set forth in SEQ ID NO: 68 and two light chains comprising an amino acid sequence set forth in SEQ ID NO: 65. In one example, the antibody binds to hG-CSFR and neutralizes G-CSF signaling.

Reference herein to a protein or antibody that "binds to" hG-CSFR provides literal support for a protein or antibody that "binds specifically to" hG-CSFR.

In one example, a protein or antibody described herein does not significantly bind to mouse G-CSFR and/or does not detectably bind to mouse G-CSFR.

In one example, a protein or antibody described herein according to any example competitively inhibits binding of C1.2 and/or C1.2G to hG-CSFR or a cell expressing same or SEQ ID NO: 1 or a soluble hG-CSFR (e.g., comprising amino acids 1-311 of SEQ ID NO: 1 fused to a Fc region of an antibody).

In one example, a protein or antibody described herein binds to a ligand binding region of hG-CSFR and a ligand binding region of cynoG-CSFR with similar affinity. In one example, the protein binds to soluble hG-CSFR and soluble cynoG-CSFR with similar affinity. In one example, the protein binds to a polypeptide comprising SEQ ID NO: 1 and to a polypeptide comprising SEQ ID NO: 67 with similar affinity. In one example, the protein binds to hG-CSFR-Fc and cynoG-CSFR-Fc as described herein with similar affinity. In one example, the affinity is at least about 2 nM, for example, at least about 1.5 nM, such as at least about 1.2 nM, 1.1 nM or 1 nM. In one example, the 0.5 nM, such as, at least about 0.46 nM or 0.45 nM or 0.40 nM or 0.39 nM. In another example, the affinity is at least about 0.1 nM, such as at least about 0.09 nM, for example, at least about 0.08 nM. In one example, the level of binding is assessed using a biosensor, e.g., by surface plasmon resonance. For example, the ligand binding region or soluble hG-CSFR or soluble cynoG-CSFR or hG-CSFR-Fc or cyno-G-CSFR-Fc is immobilized and the level of binding to a protein of the disclosure is determined In another example, the protein of the disclosure is immobilized on, for example, a biosensor and the level of binding of the ligand binding region or soluble hG-CSFR or soluble cynoG-CSFR or hG-CSFR-Fc or cyno-G-CSFR-Fc is determined For example, the level of binding to the extracellular domain of hG-CSFR or cynoG-CSFR is determined. In accordance with this example, the affinity of the protein for the extracellular domain of cynoG-CSFR is at least about 1 nM, such as at least about 0.9 nM, for example, at least about 0.75 nM. For example, the affinity is at least about 0.7 nM, such as at least about 0.6 nM, for example, at least about 0.5 nM. In one example, the affinity is about 0.5 nM. Alternatively, or additionally, the affinity of the protein for the extracellular domain of hG-CSFR is at least about 7 nM or 6 nM or 5 nM, such as at least about 4 nM, for example, at least about 3 nM, e.g., at least about 2.5 nM. For example, the affinity is at least about 2.4 or 2.5 nM.

The present disclosure also provides antigen binding domains or antigen binding fragments of the foregoing antibodies.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington D.C. United States Department of Health and Human Services, 1987 and/or 1991)).

The C-terminal lysine of the heavy chain constant region of a whole antibody of the disclosure may be removed, for example, during production or purification of the antibody, or by recombinantly engineering the nucleic acid encoding a heavy chain of the antibody. Accordingly, whole antibodies may comprise antibody populations with all C-terminal lysine residues removed, antibody populations with no C-terminal lysine residues removed, and antibody populations having a mixture of antibodies with and without the C-terminal lysine residue. In some examples, the antibody populations may additionally comprise antibodies in which the C-terminal lysine residue is removed in one of the heavy chain constant regions. Similarly, a composition of whole antibodies may comprise the same or a similar mix of antibody populations with or without the C-terminal lysine residue.

In one example, the stabilized constant region comprises a sequence from position 119 to position 445 of SEQ ID NO: 64. In one example, the stabilized constant region comprises a sequence from position 119 to position 444 of SEQ ID NO: 68. In one example a protein or antibody as described herein or a composition of a protein or antibody as described herein, comprises a heavy chain constant region, including a stabilized heavy chain constant region, comprising a mixture of sequences fully or partially with or without the C-terminal lysine residue.

In one example, an antibody of the disclosure comprises a $V_H$ disclosed herein linked or fused to an IgG4 constant region or stabilized IgG4 constant region (e.g., as discussed above) and the $V_L$ is linked to or fused to a kappa light chain constant region.

The present disclosure also provides a protein or antibody which inhibits G-CSF-induced proliferation of a BaF3 cell expressing hG-CSFR with an $IC_{50}$ of at least about 6 nM. For example, the $IC_{50}$ is 5.9 nM or less. In another example, the $IC_{50}$ is 2 nM or less or 1 nM or less or 0.7 nM or less or 0.6 nM or less or 0.5 nM or less. In one example, the $IC_{50}$ is determined by culturing BaF3 cells (e.g. about $2\times10^4$ cells) in the presence of about 0.5 ng/ml hG-CSF, e.g., for about 48 hours. In one example, the proliferation of the BaF3 cells is determined by measuring 3-(4,5-Dimethylthiazol-2-yl)-2,5-diphenyltetrazolium bromide (MTT) reduction.

The present disclosure also provides a protein or antibody which inhibits G-CSF-induced proliferation of a BaF3 cell expressing hG-CSFR with an $IC_{50}$ of at least about 10 µg/ml. For example, the $IC_{50}$ is 5 µg/ml or less. In another example, the $IC_{50}$ is 3 µg/ml or less or 2 µg/ml or less or 1 µg/ml or less. In one example, the $IC_{50}$ is about 0.8 µg/ml. In one example, the $IC_{50}$ is determined by culturing BaF3 cells (e.g. about $1\times10^4$ cells) in the presence of about 10 ng/ml hG-CSF, e.g., for about 48 hours. In one example, the proliferation of the BaF3 cells is determined by measuring $^3$H-thymidine incorporation.

In one example, a protein or antibody of the disclosure binds to a soluble hG-CSFR comprising amino acid 1-311 of SEQ ID NO: 1 expressed as a fusion with an antibody Fc region (hG-CSFR-Fc) with an affinity of at least about 1.5 nM. For example, the affinity is at least about 0.5 nM or 0.4 nM or 0.35 nM or 0.33 nM. In one example, the affinity of the protein is determined using a biosensor, e.g., by surface plasmon resonance. For example, the hG-CSFR-Fc is immobilized and the affinity of the protein of the disclosure is determined.

In one example, a protein or antibody of the disclosure binds to hG-CSFR expressed on the surface of a cell at an affinity of at least about 1 nM, for example, at least about 0.5 nM, such as, at least 0.4 nM, for example, at least 0.3 nM, such as, at least 0.2 nM.

In one example, a protein as described herein according to any example is capable of reducing the number of neutrophils in circulation when or if administered to a cynomolgus monkey. For example, the protein reduces the number of neutrophils in circulation when or if administered to a cynomolgus monkey at a dose of between 0.05 m/kg-30 mg/kg, preferably between 0.1 mg/kg-10 mg/kg, e.g., administered at a dose of 0.1 mg/kg or 1 mg/kg or 2 mg/kg or 5 mg/kg or 10 mg/kg. For example, the protein reduces the number of neutrophils in circulation when or if administered following administration of G-CSF or filgrastim or a PEGylated form thereof, e.g., when or if the protein is administered about 12 hours after administration of G-CSF or filgrastim or a PEGylated form thereof. In one example, the reduction is a 2 fold or 3 fold reduction. In one example, the neutrophils are reduced about 10-24 hours, e.g., about 12 hours following administration.

In one example, a protein or antibody as described herein is isolated and/or recombinant.

In one example, a protein or antibody of the disclosure is conjugated to another compound, for example, a detectable label or a compound that extends the half-life of the protein or antibody, such as polyethylene glycol or an albumin binding protein.

The present disclosure also provides a nucleic acid encoding the protein or antibody of the present disclosure.

In one example, such a nucleic acid is included in an expression construct in which the nucleic acid is operably linked to a promoter. Such an expression construct can be in a vector, e.g., a plasmid.

In examples of the disclosure directed to single polypeptide chain proteins, the expression construct may comprise a promoter linked to a nucleic acid encoding that polypeptide chain.

In examples directed to multiple polypeptide chains that form a protein, an expression construct comprises a nucleic acid encoding a polypeptide comprising, e.g., a $V_H$ operably linked to a promoter and a nucleic acid encoding a polypeptide comprising, e.g., a $V_L$ operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,
wherein the first polypeptide comprises a $V_H$ and the second polypeptide comprises a $V_L$, or vice versa.

The present disclosure also contemplates separate expression constructs one of which encodes a first polypeptide comprising a $V_H$ and another of which encodes a second polypeptide comprising a $V_L$. For example, the present disclosure also provides a composition comprising:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

The present disclosure also provides an isolated or recombinant cell expressing a protein of the disclosure.

In one example, the cell comprises the expression construct of the disclosure or:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

Examples of cells of the present disclosure include bacterial cells, yeast cells, insect cells or mammalian cells.

The present disclosure additionally provides methods for producing a protein or antibody of the disclosure. For example, such a method involves maintaining the expression construct(s) of the disclosure under conditions sufficient for the protein to be produced.

In one example, a method for producing a protein or antibody of the disclosure comprises culturing the cell of the disclosure under conditions sufficient for the protein or antibody to be produced and, optionally, secreted.

In one example, the method for producing a protein of the disclosure additionally comprises isolating the protein or antibody and, optionally, formulating the protein or antibody into a pharmaceutical composition.

The present disclosure additionally provides a composition comprising a protein or antibody of the disclosure and a pharmaceutically acceptable carrier.

The present disclosure additionally provides a composition comprising:
(i) an antibody comprising a heavy chain comprising an amino acid sequence set forth in SEQ ID NO: 64 and a light chain comprising an amino acid sequence set forth in SEQ ID NO: 65; and
(ii) (a) an antibody comprising a heavy chain comprising an amino acid sequence set forth in SEQ ID NO: 64 and a light chain comprising an amino acid sequence set forth in SEQ ID NO: 65; and/or
(b) an antibody comprising one heavy chain comprising an amino acid sequence set forth in SEQ ID NO: 64 and one heavy chain comprising an amino acid sequence set forth in SEQ ID NO: 68 and two light chains comprising an amino acid sequence set forth in SEQ ID NO: 65,
and, optionally, a pharmaceutically acceptable carrier.

The present disclosure also provides a method for treating or preventing a G-CSF-mediated condition in a subject, the method comprising administering the protein, antibody or composition of the disclosure. In this regard, a protein, antibody or composition can be used to prevent a relapse of a condition, and this is considered preventing the condition.

In one example, the G-CSF-mediated condition is an autoimmune disease, an inflammatory disease or cancer. For example, the autoimmune disease or the inflammatory disease is arthritis, multiple sclerosis, pulmonary inflammation or chronic obstructive pulmonary disease.

In one example, the method comprises administering an amount of the protein or antibody sufficient to reduce the number of neutrophils in a subject without inducing neutropenia.

The present disclosure alternatively or additionally provides a method for reducing the number of neutrophils in a subject without inducing neutropenia, the method comprising administering a protein comprising an antigen binding site of an antibody that binds (or specifically binds) to hG-CSFR to the subject. An exemplary protein is an antibody or comprises an antigen binding domain thereof (e.g., a $V_H$ and/or a $V_L$) or is an antigen binding fragment thereof. Exemplary proteins and antibodies are described herein.

In one example, a method described herein comprises administering an amount of the protein or antibody sufficient to reduce the number of neutrophils in a subject without inducing moderate neutropenia.

In one example, a method described herein comprises administering an amount of the protein or antibody sufficient to reduce the number of neutrophils in a subject without inducing severe neutropenia.

In one example, a method described herein comprises administering between about 0.05 mg/kg and 30 mg/kg of the protein or antibody. For example, the method comprising administering between 0.1 mg/kg and 10 mg/kg or between 0.2 mg/kg and 5 mg/kg of the protein or antibody. In one example, the method comprises administering about 0.5-2.0 mg/kg of the protein or antibody.

The present disclosure also provides for use of a protein or antibody as described herein in any example in medicine.

The present disclosure also provides for use of a protein or antibody as described herein according to any example in the manufacture of a medicament to treat a G-CSF-mediated condition.

The present disclosure also provides a method for localizing and/or detecting and/or diagnosing and/or prognosing G-CSF-mediated condition associated with a cell expressing G-CSFR, the method comprising detecting in vivo a protein or antibody as described herein bound to the G-CSFR expressing cell, if present, wherein the protein or antibody is conjugated to a detectable tag.

In one example, the method additionally comprises administering the protein to the subject.

The present disclosure also provides a method for detecting G-CSFR or a cell expressing same in a sample, the method comprising contacting the sample with a protein or antibody as described herein according to any example such that a complex forms and detecting the complex, wherein detection of the complex is indicative of G-CSFR or a cell expressing same in the sample.

The present disclosure also provides a method for diagnosing or prognosing a G-CSF-mediated condition, the method comprising performing a method as described herein according to any example to detect G-CSFR or a cell expressing same, wherein detection of the G-CSFR or cell expressing same is diagnostic or prognostic of the condition.

The present disclosure also provides a kit comprising a protein or antibody as described herein according to any example packaged with instructions for use in a method as described herein.

Key to Sequence Listing
SEQ ID NO: 1—amino acids 25-335 of *Homo sapiens* G-CSFR (hG-CSFR) with a C-terminal polyhistidine tag
SEQ ID NO: 2—$V_H$ of C1.2
SEQ ID NO: 3—$V_L$ of C1.2
SEQ ID NO: 4—$V_H$ of C1.2G
SEQ ID NO: 5—$V_L$ of C1.2G
SEQ ID NO: 6—HCDR1 of C1.2
SEQ ID NO: 7—HCDR2 of C1.2
SEQ ID NO: 8—HCDR3 of C1.2
SEQ ID NO: 9—LCDR1 of C1.2
SEQ ID NO: 10—LCDR2 of C1.2
SEQ ID NO: 11—LCDR3 of C1.2
SEQ ID NO: 12—consensus sequence of HCDR3 of C1.2
SEQ ID NO: 13—consensus sequence of LCDR3 of C1.2
SEQ ID NO: 14—$V_L$ of antibody 987
SEQ ID NO: 15—$V_H$ of antibody 987
SEQ ID NO: 16—$V_L$ of antibody 95
SEQ ID NO: 17—$V_L$ of antibody 79
SEQ ID NO: 18—$V_L$ of antibody 83
SEQ ID NO: 19—$V_L$ of antibody 1003
SEQ ID NO: 20—$V_H$ of antibody 1003
SEQ ID NO: 21—$V_L$ of antibody 44
SEQ ID NO: 22—$V_L$ of antibody 97
SEQ ID NO: 23—$V_L$ of antibody 986
SEQ ID NO: 24—$V_H$ of antibody 986
SEQ ID NO: 25—$V_L$ of antibody 56
SEQ ID NO: 26—$V_L$ of antibody 77
SEQ ID NO: 27—$V_L$ of antibody 54
SEQ ID NO: 28—$V_H$ of antibody 54
SEQ ID NO: 29—$V_L$ of antibody 802
SEQ ID NO: 30—$V_L$ of antibody 967
SEQ ID NO: 31—$V_H$ of antibody 967
SEQ ID NO: 32—$V_L$ of antibody 989
SEQ ID NO: 33—$V_H$ of antibody 989
SEQ ID NO: 34—$V_L$ of antibody 63
SEQ ID NO: 35—$V_L$ of antibody 1002
SEQ ID NO: 36—$V_H$ of antibody 1002
SEQ ID NO: 37—$V_L$ of antibody 994
SEQ ID NO: 38—$V_H$ of antibody 994
SEQ ID NO: 39—$V_L$ of antibody 969
SEQ ID NO: 40—$V_H$ of antibody 969
SEQ ID NO: 41—$V_L$ of antibody 1000
SEQ ID NO: 42—$V_H$ of antibody 1000
SEQ ID NO: 43—$V_L$ of antibody 94
SEQ ID NO: 44—$V_L$ of antibody 975
SEQ ID NO: 45—$V_H$ of antibody 975
SEQ ID NO: 46—$V_L$ of antibody 75
SEQ ID NO: 47—$V_L$ of antibody 814
SEQ ID NO: 48—$V_L$ of antibody 973
SEQ ID NO: 49—$V_H$ of antibody 973
SEQ ID NO: 50—$V_L$ of antibody 977
SEQ ID NO: 51—$V_H$ of antibody 977
SEQ ID NO: 52—$V_L$ of antibody 984
SEQ ID NO: 53—$V_H$ of antibody 984
SEQ ID NO: 54—$V_L$ of antibody 61
SEQ ID NO: 55—$V_H$ of antibody 852
SEQ ID NO: 56—$V_L$ of antibody 996
SEQ ID NO: 57—$V_H$ of antibody 996
SEQ ID NO: 58—$V_L$ of antibody 43
SEQ ID NO: 59—$V_H$ of antibody 43
SEQ ID NO: 60—$V_L$ of antibody 999
SEQ ID NO: 61—$V_H$ of antibody 999
SEQ ID NO: 62—$V_L$ of antibody 870
SEQ ID NO: 63—$V_L$ of antibody 877
SEQ ID NO: 64—Heavy chain of C1.2G with stabilized IgG4 constant region
SEQ ID NO: 65—Light chain of C1.2G with kappa constant region
SEQ ID NO: 66—sequence of exemplary h-GCSFR
SEQ ID NO: 67—polypeptide comprising Ig and CRH domains of *Macaca fascicularis* G-CSFR (cynoG-CSFR) with a C-terminal polyhistidine tag
SEQ ID NO: 68—Heavy chain of C1.2G with stabilized IgG4 constant region and lacking C-terminal lysine.

BRIEF DESCRIPTION OF THE DRAWINGS

FIG. 2B is a graphical representation showing the relative binding of C1.2G, mAb744 and mAb774 to a series of alanine point mutants of SEQ ID NO: 1 compared to their binding to SEQ ID NO: 1 (positions of mutations are indicated with reference to SEQ ID NO: 1). The fold decrease in $K_D$ of the antibody for the mutant receptor compared to SEQ ID NO: 1 is depicted.

DETAILED DESCRIPTION

General

Figure 1:
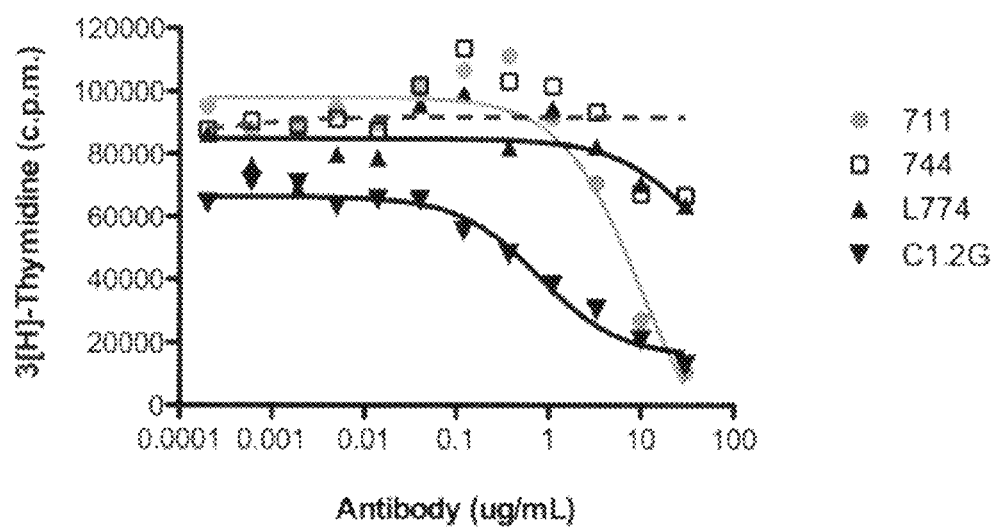
FIG. 1 is a graphical representation showing inhibition of G-CSF-mediated proliferation of BaF3 cells by increasing concentrations of various anti-G-CSFR antibodies. The relative $IC_{50}$ values for each antibody were; 10.1 μg/mL for mAb711, 37.4 μg/ml for mAb 774, 0.8 μg/mL for C1.2G and was not determinable for mAb 744.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

For the purposes of nomenclature only and not limitation an exemplary sequence of a human G-CSFR is set out in NCBI Reference Sequence: NP_000751.1 (and set out in SEQ ID NO: 66). The sequence of cynomolgus monkey G-CSFR can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human G-CSFR may be abbreviated to hG-CSFR and reference to cynomolgus monkey G-CSFR may be abbreviated to cynoG-CSFR. Reference to soluble G-CSFR refers to polypeptides comprising the ligand binding region of G-CSFR. The Ig and CRH domains of the G-CSFR are involved in ligand binding and receptor dimerization (Layton et al., *J. Biol Chem.*, 272: 29735-29741, 1997 and Fukunaga et al, *EMBO J.* 10: 2855-2865, 1991). Soluble forms of G-CSFR comprising these portions of the receptor have been used in various studies of the receptor and mutation of the free cysteines at positions 78, 163, and 228 of the receptor assists in expression and isolation of the soluble receptor polypeptide (Mine et al., *Biochem.*, 43: 2458-2464 2004) without affecting ligand binding. In the present studies soluble forms of the receptor comprising amino acids 25-335 of hG-CSFR with mutations C78A, C163S and C228S were used (e.g. SEQ ID NO:1) and the corresponding segment of cynoG-CSFR with the cysteine mutations was used (e.g., SEQ ID NO 67) for studies on the cynomolgus monkey receptor. Various point mutations of the soluble receptor of SEQ ID NO:1 and SEQ ID NO: 67 have also been utilized. Reference to hG-CSFR-Fc means the polypeptide of SEQ ID NO:1 wherein the C-terminal polyhistidine tag has been replaced with an Fc sequence (e.g., a polypeptide comprising amino acids 1-311 of SEQ ID NO: 1 fused to an Fc). cynoG-CSFR-Fc means the corresponding segment of cynoG-CSFR with an Fc sequence attached to its C-terminus (e.g., a polypeptide comprising amino acids 1-311 of SEQ ID NO: 67 fused to an Fc). The inventors have shown that antibodies and proteins comprising antigen binding sites thereof (e.g., Fab) bind to wild type hG-CSF polypeptides and to these mutant proteins with highly similar affinity. Accordingly, studies using the mutant proteins are a model of studies using hG-CSFR and/or cynoG-CSFR.

Reference herein to G-CSF includes native forms of G-CSF, mutant forms thereof, e.g., filgrastim and pegylated forms of G-CSF or filgrastim. This term also encompasses mutant forms of G-CSF retaining activity to bind to G-CSFR (e.g., hG-CSFR) and induce signaling.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site is a $V_H$ or a $V_L$ or a Fv.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., IgG$_1$, IgG$_2$, IgG$_3$, IgG$_4$, IgA$_1$ and IgA$_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Pliikthun *J. Mol. Biol.*, 309: 657-670, 2001. For example, according to the numbering system of Kabat, $V_H$ framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab₂" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to G-CSFR (e.g., hG-CSFR) with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). In an example of the present disclosure, a protein that "specifically binds" to one form of hG-CSFR or a polypeptide comprising a region thereof (e.g., the ligand binding domain of hG-GCSFR) or a polypeptide comprising amino acids 1-311 of SEQ ID NO: 1 with an affinity at least 20 fold or 40 fold or 60 fold or 80 fold or 100 fold or 150 fold or 200 fold greater than it does to a mutant form of hG-CSFR or a polypeptide comprising a region thereof (e.g., a mutant form of the ligand binding domain of h-GCSFR) or a mutant form of SEQ ID NO: 1 comprising an alanine substituted for the native arginine at position 287. Additional exemplary changes to SEQ ID NO: 1 and their effect on binding are described herein. Generally, but not necessarily, reference to binding means specific binding, and each term shall be understood to provide explicit support for the other term.

As used herein, the term "does not detectably bind" shall be understood to mean that a protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the protein is immobilized and contacted with an antigen.

As used herein, the term "does not significantly bind" shall be understood to mean that the level of binding of a protein of the disclosure to a polypeptide is not statistically significantly higher than background, e.g., the level of binding signal detected in the absence of the protein and/or in the presence of a negative control protein (e.g., an isotype control antibody) and/or the level of binding detected in the presence of a negative control polypeptide. The level of binding is detected using biosensor analysis (e.g. Biacore) in which the protein is immobilized and contacted with an antigen.

As used herein, phrases referring to "reduced binding" or "binding being at a lower level" in relation to an antigen will be understood to mean that an antibody binds to an antigen (e.g., an alanine point mutant of SEQ ID NO:1 at any one of positions 287, 237, 198, 172, 171 or 111) with an affinity at least about 20 fold or 40 fold or 60 fold less than a control epitope or antigen (e.g. SEQ ID NO:1). For example, a protein of the present disclosure can bind to a polypeptide of SEQ ID NO: 1 in which an alanine is substituted for the histidine at position 237 at a level 20 fold or 40 fold or 60 fold less than it binds to a polypeptide of SEQ ID NO: 1. Preferably, the protein binds at a level 20 fold less, more preferably 40 fold less, still more preferably 60 fold less.

A protein or antibody may be considered to "preferentially bind" to a polypeptide if it binds that polypeptide with a dissociation constant ($K_D$) that is less than the protein's or antibody's $K_D$ for another polypeptide. In one example, a protein or antibody is considered to preferentially bind to a polypeptide if it binds the polypeptide with an affinity (i.e., $K_D$) that is at least about 20 fold or 40 fold or 60 fold or 80 fold or 100 fold or 120 fold or 140 fold or 160 fold more than the protein's or antibody's $K_D$ for another polypeptide.

As used herein, the term "similar affinity" will be understood to mean that a protein of the present disclosure binds to two antigens (e.g., the ligand binding domain of G-CSFR from humans and from cynomolgus monkeys) with affinities that are within about 5 fold or less of one another, e.g., within about 4, 3, 2, or 1 fold of one another, such as, within about 0.5 fold of one another or the levels of binding are substantially identical, e.g., when the affinity is assessed by immobilizing the two antigens (e.g., the ligand binding domain of G-CSFR or extracellular domains from humans and from cynomolgus monkeys) and contacting the immobilized proteins with a protein of the disclosure.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or greater (i.e., the value recited as the $IC_{50}$ is lower), i.e., an $IC_{50}$ of 2 nM is greater than an $IC_{50}$ of 3 nM. Stated another way, this term could be "an $IC_{50}$ of X or less", wherein X is a value recited herein.

As used herein, the term "epitope" (syn. "antigenic determinant") shall be understood to mean a region of hG-CSFR to which a protein comprising an antigen binding site of an antibody binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when hG-CSFR is folded, i.e., a "conformational epitope". For example, a conformational epitope comprises amino acids in one or more or two or more or all of the regions corresponding to 111-115, 170-176, 218-234 and/or 286-300 of SEQ ID NO: 1. The skilled artisan will also be aware that the term "epitope" is not limited to peptides or polypeptides. For example, the term "epitope"

includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to G-CSFR, e.g., to hG-CSFR. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to G-CSFR either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a protein is capable of blocking, reducing or preventing G-CSF-mediated signaling in a cell through the G-CSFR. Methods for determining neutralization are known in the art and/or described herein.

As used herein, the term "condition" refers to a disruption of or interference with normal function, and is not to be limited to any specific condition, and will include diseases or disorders.

As used herein, a "G-CSF-associated condition" refers to any condition that is caused by or associated with neutrophils, an excess of G-CSF or cells expressing G-CSFR or with administration of G-CSF. The skilled artisan will be readily able to determine such conditions. In this regard, in some examples the condition is an inflammatory condition, an autoimmune condition or cancer (including metastasis).

As used herein, the terms "preventing", "prevent" or "prevention" include administering a protein of the disclosure to thereby stop or hinder the development of at least one symptom of a condition. This term also encompasses treatment of a subject in remission to prevent or hinder relapse. For example, a subject suffering from relapsing-remitting multiple sclerosis is treated during remission to thereby prevent a relapse.

As used herein, the terms "treating", "treat" or "treatment" include administering a protein described herein to thereby reduce or eliminate at least one symptom of a specified disease or condition.

As used herein, the term "neutropenia" will be understood to encompass mild neutropenia (1000<=ANC<1500), moderate neutropenia (500<=ANC<1000) and Severe neutropenia (ANC<500) (absolute neutrophil count (ANC) measured in cells per microliter of blood).

As used herein, the term "subject" shall be taken to mean any animal including humans, for example a mammal. Exemplary subjects include but are not limited to humans and non-human primates. For example, the subject is a human.

Antibodies

In one example, a protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods G-CSFR (e.g., hG-CSFR) or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mabs).

Monoclonal antibodies are one exemplary form of antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies and, for example, do not express murine antibodies, can also be used to generate an antibody of the present disclosure (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemistry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

As described herein, some proteins of the present disclosure that bind hG-CSFR cross-react with cynoG-CSFR and/or bind to some mutant forms of hG-CSFR or polypeptides comprising regions of hG-CSFR that have been mutated and/or not others and/or bind to a specific epitope within hG-CSFR. These characteristics can be used in the generation of an antibody or a protein comprising a binding site thereof.

For example, a phage display library is screened with a polypeptide comprising the ligand binding domain of hG-CSFR to identify proteins that bind thereto. Mutant forms of the ligand binding domain of hG-CSFR (e.g., an alanine point mutant of SEQ ID NO:1 at position 287) to which the protein is not to detectably bind are then used to remove cross-reactive proteins and mutant forms of the ligand binding domain of hG-CSFR or regions thereof (e.g., an alanine point mutant of SEQ ID NO:1 at position 168) to which the protein is to bind are used to isolate proteins that are correctly cross-reactive. A screening process for immunization of a non-human mammal can also be devised based on the foregoing.

In another example, a phage display library is screened or an animal is immunized with a polypeptide comprising the ligand binding domain of cynoG-CSFR and identified proteins and/or antibodies are screened to identify those that are cross-reactive with hG-CSFR and/or the ligand binding domain thereof.

In a further example, a G-CSFR or a ligand binding domain thereof (optionally a mutant form to which C1.2 or C1.2G binds) is contacted with C1.2 or C1.2G. A phage display library is then brought into contact with the G-CSFR or the ligand binding domain and phage expressing proteins that can compete with C1.2 or C1.2G for binding selected.

In a still further example, a chimeric protein comprising, e.g., a mouse G-CSFR in which an epitope of interest from a hG-CSFR is substituted for the corresponding mouse sequence. This chimeric protein is then used to immunize mice (which are less likely to induce an immune response against the mouse protein) and/or to screen a phage display library. The resulting antibodies/proteins are then screened to identify those that bind to hG-CSFR (particularly at the epitope of interest) and not mouse G-CSFR.

The antibody of the present disclosure may be a synthetic antibody. For example, the antibody is a chimeric antibody, a humanized antibody, a human antibody or a de-immunized antibody.

Chimeric Antibodies

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Typically chimeric antibodies utilize rodent or rabbit variable regions and human constant regions, in order to produce an antibody with predominantly human domains. Methods for producing chimeric antibodies are described in, e.g., U.S. Pat. No. 4,816,567; and U.S. Pat. No. 5,807,715.

Humanized and Human Antibodies

The antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. Nos. 5,225,539, or 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4, 5 or 6 of the residues of the antibody, e.g. in 1, 2, 3, 4, 5 or 6 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

Exemplary human antibodies are described herein and include C1.2 and C1.2G and/or variable regions thereof. These human antibodies provide an advantage of reduced immunogenicity in a human compared to non-human antibodies.

Antibody Binding Domain Containing Proteins

Single-Domain Antibodies

In some examples, a protein of the disclosure is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies In some examples, a protein of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Antibody Fragments

The present disclosure also contemplates other antibodies and antibody fragments, such as:

(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) $Fab_3$ (e.g., as described in EP19930302894).

De-Immunized Antibodies and Proteins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. In this regard, data presented herein indicate sites within a CDR of a protein of the disclosure that can be changed in addition to exemplary changes that can be made. The skilled person will understand that changes can additionally or alternatively be made within a FR of a variable region containing protein without inhibiting or significantly reducing its function in the context of the present disclosure.

For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), (β-branched side chains (e.g., threonine, valine, isoleucine) and aromatic side chains (e.g., tyrosine, phenylalanine, tryptophan, histidine).

The present disclosure also contemplates non-conservative amino acid changes (e.g., substitutions) in a protein of the present disclosure, e.g., in a CDR, such as CDR3. For example, the present inventors have identified several non-conservative amino acid substitutions that can be made while retaining an activity of a protein of the disclosure. In one example, the protein comprises fewer than 6 or 5 or 4 or 3 or 2 or 1 non-conservative amino acid substitutions, e.g., in a CDR3, such as in a CDR3.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to an antibody.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Protein Production

In one example, a protein described herein according to any example is produced by culturing a hybridoma under conditions sufficient to produce the protein, e.g., as described herein and/or as is known in the art.

Recombinant Expression

In another example, a protein described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, lpp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharomyces cerevisiae and S. pombe, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Assaying Activity of a Protein

Binding to G-CSFR and Mutants Thereof

It will be apparent to the skilled artisan from the disclosure herein that some proteins of the present disclosure bind to the ligand binding domain of hG-CSFR and to specific mutant forms of the ligand binding domain of hG-CSFR (e.g., SEQ ID NO: 1 without or with certain point mutations) and/or bind to both human and cynomolgus monkey G-CSFR. Methods for assessing binding to a protein are known in the art, e.g., as described in Scopes (In: Protein purification: principles and practice, Third Edition, Springer Verlag, 1994). Such a method generally involves labeling the protein and contacting it with immobilized antigen. Following washing to remove non-specific bound protein, the amount of label and, as a consequence, bound protein is detected. Of course, the protein can be immobilized and the antigen labeled. Panning-type assays can also be used. Alternatively, or additionally, surface plasmon resonance assays can be used.

The assays described above can also be used to detect the level of binding of a protein to hG-CSFR or a ligand binding domain thereof (e.g., SEQ ID NO: 1) or mutant form thereof.

In one example, a protein of the present disclosure binds to a polypeptide of SEQ ID NO: 1 in which an alanine is substituted for the lysine at position 167 of SEQ ID NO: 1 and/or in which an alanine is substituted for the histidine at position 168 of SEQ ID NO: 1 at substantially the same level (e.g., within 10% or 5% or 1%) as it binds to SEQ ID NO: 1.

In one example, a protein of the present disclosure binds to a polypeptide of SEQ ID NO: 1 in which an alanine is substituted for the arginine at position 287 of SEQ ID NO: 1 at a level at least about 100 fold or 150 fold or 160 fold or 200 fold lower than it binds to a polypeptide of SEQ ID NO: 1. In one example, a protein of the present disclosure binds to a polypeptide of SEQ ID NO: 1 in which an alanine is substituted for the arginine at position 287 of SEQ ID NO: 1 at a level at least about 160 fold lower than it binds to a polypeptide of SEQ ID NO: 1.

In one example, a protein of the present disclosure binds to a polypeptide of SEQ ID NO: 1 in which an alanine is substituted for the histidine at position 237 of SEQ ID NO: 1 at a level at least about 20 fold or 40 fold or 50 fold or 60 fold lower than it binds to a polypeptide of SEQ ID NO: 1. In one example, a protein of the present disclosure binds to a polypeptide of SEQ ID NO: 1 in which an alanine is substituted for the histidine at position 237 of SEQ ID NO: 1 at a level at least about 50 fold lower than it binds to a polypeptide of SEQ ID NO: 1.

In one example, a protein of the present disclosure binds to a polypeptide of SEQ ID NO: 1 in which an alanine is substituted for the methionine at position 198 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the methionine at position 198 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the tyrosine at position 172 of SEQ ID NO: 1 at a level at least about 20 fold or 30 fold or 40 fold lower than it binds to a polypeptide of SEQ ID NO: 1. In one example, a protein of the present disclosure binds to a polypeptide of SEQ ID NO: 1 in which an alanine is substituted for the tyrosine at position 172 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the leucine at position 171 of SEQ ID NO: 1 at a level at least about 100 fold or 120 fold or 130 fold or 140 fold lower than it binds to a polypeptide of SEQ ID NO: 1. In one example, a protein of the present disclosure binds to a polypeptide of SEQ ID NO: 1 in which an alanine is substituted for the leucine at position 171 of SEQ ID NO: 1 at a level at least about 140 fold lower than it binds to a polypeptide of SEQ ID NO: 1.

In one example, a protein of the present disclosure binds to a polypeptide of SEQ ID NO: 1 in which an alanine is substituted for the leucine at a position 111 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the leucine at a position 111 of SEQ ID NO: 1 at a level at least about 60 fold lower than it binds to a polypeptide of SEQ ID NO: 1.

In one example, a protein of the present disclosure binds to a polypeptide of SEQ ID NO: 1 in which an alanine is substituted for the histidine at position 168 of SEQ ID NO: 1 at a level no more than 5 fold or 4 fold or 3 fold or 2 fold or 1 fold lower than it binds to a polypeptide of SEQ ID NO: 1.

In one example, a protein of the present disclosure binds to a polypeptide of SEQ ID NO: 1 in which an alanine is substituted for the lysine at position 167 of SEQ ID NO: 1 at a level no more than 5 fold or 4 fold or 3 fold or 2 fold or 1 fold lower than it binds to a polypeptide of SEQ ID NO: 1.

The level of binding is conveniently determined using a biosensor.

The present disclosure contemplates any combination of the foregoing characteristics. In one example, a protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the hG-CSFR sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within hG-CSFR are mutated, e.g., by alanine scanning mutagenesis, and mutations that reduce or prevent protein binding are determined. Any mutation that reduces or prevents binding of the protein is likely to be within the epitope bound by the protein.

A further method is exemplified herein, and involves binding hG-CSFR or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in hG-CSFR or a region thereof to deutrons and binding the resulting protein to an immobilized protein of the present disclosure. The deutrons are then converted back to hydrogen, the hG-CSFR or region thereof isolated, digested with enzymes and analyzed, e.g., using mass spectrometry to identify those regions comprising deutrons, which would have been protected from conversion to hydrogen by the binding of a protein described herein.

Optionally, the dissociation constant (Kd) of a protein for hG-CSFR or an epitope thereof is determined. The "Kd" or "Kd value" for a hG-CSFR binding protein is in one example measured by a radiolabeled or fluorescently-labeled hG-CSFR binding assay. This assay equilibrates the protein with a minimal concentration of labeled G-CSF in the presence of a titration series of unlabeled hG-CSFR. Following washing to remove unbound hG-CSFR, the amount of label is determined, which is indicative of the Kd of the protein.

According to another example the Kd or Kd value is measured by using surface plasmon resonance assays, e.g., using BIAcore surface plasmon resonance (BIAcore, Inc., Piscataway, N.J.) with immobilized hG-CSFR or a region thereof.

In some examples, proteins having a similar Kd or a higher Kd than C1.2 or C1.2G are selected, because they are likely to compete for binding to hG-CSFR.

Determining Competitive Binding

Assays for determining a protein that competitively inhibits binding of monoclonal antibody C1.2 or C1.2G will be apparent to the skilled artisan. For example, C1.2 or C1.2G is conjugated to a detectable label, e.g., a fluorescent label or a radioactive label. The labeled antibody and the test protein are then mixed and contacted with hG-CSFR or a region thereof (e.g., a polypeptide comprising SEQ ID NO: 1) or a cell expressing same. The level of labeled C1.2 or C1.2G is then determined and compared to the level determined when the labeled antibody is contacted with the hG-CSFR, region or cells in the absence of the protein. If the level of labeled C1.2 or C1.2G is reduced in the presence of the test protein compared to the absence of the protein, the protein is considered to competitively inhibit binding of C1.2 or C1.2G to hG-CSFR.

Optionally, the test protein is conjugated to different label to C1.2 or C1.2G. This alternate labeling permits detection of the level of binding of the test protein to hG-CSFR or the region thereof or the cell.

In another example, the protein is permitted to bind to hG-CSFR or a region thereof (e.g., a polypeptide comprising SEQ ID NO: 1) or a cell expressing same prior to contacting the hG-CSFR, region or cell with C1.2 or C1.2G. A reduction in the amount of bound C1.2 or C1.2G in the presence of the protein compared to in the absence of the protein indicates that the protein competitively inhibits C1.2 or C1.2G binding to hG-CSFR. A reciprocal assay can also be performed using labeled protein and first allowing C1.2 or C1.2G to bind to G-CSFR. In this case, a reduced amount of labeled protein bound to hG-CSFR in the presence of C1.2 or C1.2G compared to in the absence of C1.2 or C1.2G indicates that the protein competitively inhibits binding of C1.2 or C1.2G to hG-CSFR.

Any of the foregoing assays can be performed with a mutant form of hG-CSFR and/or SEQ ID NO: 1 and/or a ligand binding region of hG-CSFR to which C1.2 or C1.2G binds, e.g., as described herein.

Determining Neutralization

In some examples of the present disclosure, a protein is capable of neutralizing hG-CSFR signaling.

Various assays are known in the art for assessing the ability of a protein to neutralize signaling of a ligand through a receptor.

In one example, the protein reduces or prevents G-CSF binding to the hG-CSFR. These assays can be performed as a competitive binding assay as described herein using labeled G-CSF and/or labeled protein.

In another example, the protein reduces formation of CFU-G when $CD34^+$ bone marrow cells are cultured in the presence of G-CSF. In such assays, $CD34^+$ bone marrow cells are cultured in a semi-solid cell culture medium in the presence of G-CSF (e.g., about 10 ng/ml cell culture medium) and, optionally stem cell factor (e.g., about 10 ng/ml cell culture medium) in the presence or absence of a test protein. After a sufficient time for granulocyte clones (CFU-G) to form, the number of clones or colonies is determined. A reduction in the number of colonies in the presence of the protein compared to in the absence of the protein indicates that the protein neutralizes G-CSF signaling. By testing multiple concentrations of the protein an $IC_{50}$ is determined, i.e., a concentration at which 50% of the maximum inhibition of CFU-G formation occurs. In one example, the $IC_{50}$ is 0.2 nM or less, such as 0.1 nM or less, for example, 0.09 nM or less, or 0.08 nM or less, or 0.07 nM or less, or 0.06 nM or less or 0.05 nM or less. In one example, the $IC_{50}$ is 0.04 nM or less. In another example, the $IC_{50}$ is 0.02 nM or less. The foregoing $IC_{50}$s relate to any CFU-G assay described herein.

In a further example, the protein reduces proliferation of cells (e.g., BaF3 cells) expressing hG-CSFR which are cultured in the presence of G-CSF. Cells are cultured in the presence of G-CSF (e.g., 0.5 ng/ml) and the presence or absence of a test protein. Methods for assessing cell proliferation are known in the art and include, for example, MTT reduction and thymidine incorporation. A protein that reduces the level of proliferation compared to the level observed in the absence of the protein is considered to neutralize G-CSF signaling. By testing multiple concentrations of the protein an $IC_{50}$ is determined, i.e., a concentration at which 50% of the maximum inhibition of cell proliferation occurs. In one example, the $IC_{50}$ is 6 nM or less, such as 5.9 nM or less. In another example, the $IC_{50}$ is 2 nM or less or 1 nM or less or 0.7 nM or cell or 0.6 nM or less or 0.5 nM or less. The foregoing $IC_{50}$s relate to any cell proliferation assay described herein.

In a further example, the protein reduces mobilization of hematopoietic stem cells and/or endothelial progenitor cells in vivo following G-CSF administration and/or reduces the number of neutrophils in vivo, e.g., following G-CSF administration (however this is not essential). For example, the protein is administered to a subject, optionally before, at the time of or after administration of G-CSF or a modified form thereof (e.g., PEGylated G-CSF or filgrastim). The number of hematopoietic stem cells (e.g., expressing CD34 and/or Thy1) and/or endothelial progenitor cells (e.g., expressing CD34 and VEGFR2) and/or neutrophils (identified morphologically and/or expressing e.g., CD10, CD14, CD31 and/or CD88) is assessed. A protein that reduces the level of the cell(s) compared to the level observed in the absence of the protein is considered to neutralize G-CSF signaling. In one example, the protein reduces the number of neutrophils without inducing neutropenia.

Other methods for assessing neutralization of G-CSF signaling are contemplated by the present disclosure.

Determining Effector Function

As discussed herein, some proteins of the present disclosure have reduced effector function. Methods for assessing ADCC activity are known in the art.

In one example, the level of ADCC activity is assessed using a $^{51}$Cr release assay, an europium release assay or a $^{35}$S release assay. In each of these assays, cells expressing G-CSFR are cultured with one or more of the recited compounds for a time and under conditions sufficient for the compound to be taken up by the cell. In the case of a $^{35}$S release assay, cells expressing hG-CSFR can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the protein compared to in the absence of protein (or a reduced level of the compound compared to the level observed in the presence of an anti-hG-CSFR antibody comprising a human IgG1 Fc) indicates that the protein has reduced effector function. Exemplary publications disclosing assays for assessing the level of ADCC induced by a protein include Hellstrom, et al. *Proc. Natl. Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, Wis., USA).

C1q binding assays may also be carried out to confirm that the protein is able to bind C1q and may induce CDC. To assess complement activation, a CDC assay may be performed (see, for example, Gazzano-Santoro et al, *J. Immunol. Methods* 202: 163, 1996.

Determining Half Life

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Assessing Therapeutic Efficacy

Assays for assessing therapeutic efficacy are described hereinabove in relation to determining neutralization by a protein.

In another example, the efficacy of a protein to treat a condition is assessed using an in vivo assay.

For example, the protein is tested in an animal model of arthritis. Exemplary models include a SKG strain of mouse (Sakaguchi et al., Nature, 426: 454-460), rat type II collagen arthritis model, mouse type II collagen arthritis model or antigen induced arthritis models in several species (Bendele *J Musculoskel Neuron Interact;* 1(4):377-385, 2001). In these assays, arthritis is induced and the ability of the protein to reduce one or more symptoms of arthritis, e.g., joint inflammation and/or markers of inflammation in synovial fluid is assessed. A protein that reduces a symptom of arthritis is considered useful for treating this condition or a G-CSF-mediated condition (e.g., a G-CSF-mediated inflammatory condition).

The protein can also or alternatively be tested in a model of COPD, e.g., in which a non-human mammal (e.g., a rodent, such as, a mouse) is exposed to cigarette smoke. Following exposure, the mammal is administered a protein and the level of lung inflammation and/or the number of neutrophils in the lung is assessed or estimated using standard techniques. A protein that reduces lung inflammation and/or the number of neutrophils is considered useful for treating lung inflammation or COPD or a G-CSF-mediated condition (e.g., a G-CSF-mediated inflammatory condition, such as a G-CSF-mediated inflammatory lung condition).

Proteins described herein can also tested in in vivo models of inflammatory neurological disease. Exemplary models include EAE models in which a mouse or rat is immunized with a myelin sheath protein or peptide derived therefrom (e.g., MOG, MBP or PLP) and an immune response is generated against the protein thereby inducing a model of MS. Alternatively, T cells that are immunoreactive with a myelin sheath protein are introduced into mice or rats to induce EAE. Exemplary EAE models are reviewed in, for example Tsunoda and Fujinami, *J Neuropathol Exp Neurol.* 55:673-686, 1996.

Other models of MS include transgenic animals expressing T cell receptors specific for a myelin protein, e.g., MOG, MBP or PLP. Exemplary models are described, for example, in Bettelli et al., *JEM* 197:1073-1081, 2003; Illés et al., *Proc. Natl. Acad. Sci. USA*, 101: 11749-11754, 2004; or Rossi et al., *J. Biomolecular Screening*, 12: 481-489, 2007; or are commercially available, e.g., from Jackson Laboratories USA (e.g. mice 2D2 having transgenic T cell receptors reactive with MOG).

In a further example, a protein described herein according to any example is tested in a model of uveitis. Models of uveitis include those induced by immunizing a non-human mammal with a protein such as retinal arrestin, recoverin or rhodopsin or administration of bacterial endotoxin to eye. Exemplary models of uveitis are described, for example, in Caspi, *Drug Discovery Today*, 3: 3-9, 2006.

A protein of the disclosure can also be tested in models of angiogenesis, e.g., Iris Pharma Inc's models of ocular angiogenesis, or an alginate encapsulated tumor cell model, and/or by assessing the ability of a cancer cell to metastasize in a subject.

Conditions to be Treated

The present disclosure contemplates treatment or prevention of any condition that is caused by or exacerbated by G-CSF in a subject. In one example, the condition is an autoimmune or inflammatory condition.

In one example, the inflammatory or autoimmune condition is an inflammatory joint condition, such as, inflammatory arthritis, rheumatoid arthritis or idiopathic arthritis, e.g., juvenile idiopathic arthritis. In one example, the condition is rheumatoid arthritis.

In one example, the inflammatory or autoimmune condition is an inflammatory eye condition. For example, the condition is uveitis.

In one example, the inflammatory or autoimmune condition is an inflammatory lung condition, such as, a pulmonary disease associated with neutrophil infiltration, e.g., COPD. In one example, the condition is COPD.

In one example, the inflammatory or autoimmune condition is an inflammatory neurological condition, such as, Devic's disease, a viral infection in the brain or multiple sclerosis. In one example, the condition is multiple sclerosis, which includes chronic progressive multiple sclerosis or relapsing-remitting multiple sclerosis.

In another example, the condition is cancer (including angiogenesis thereof) or metastasis thereof.

In one example, the subject is resistant to, does not adequately respond to, or is unsuitable for treatment with another compound used to treat the condition. For example, the subject suffering from an autoimmune or inflammatory condition is resistant to, does not adequately respond to, or is unsuitable for treatment with a corticosteroid and/or an immunosuppressant and/or cyclophosphamide and/or methotrexate and/or an anti-TNF antibody or soluble TNF receptor and/or an anti-CD20 antibody and/or an anti-IL6 antibody and/or an anti-CD22 antibody.

Compositions

In some examples, a protein as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing a protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or administration into a body cavity or lumen of an organ or joint. The compositions for administration will commonly comprise a solution of protein dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, proteins of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

WO2002/080967 describes compositions and methods for administering aerosolized compositions comprising antibodies for the treatment of, e.g., asthma, which are also suitable for administration of a protein of the present disclosure.

Combination Therapies

In one example, a protein of the present disclosure is administered in combination with another compound useful for treating a disease or condition described herein, either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is methotrexate. Alternatively, or additionally, the other compound is cyclophosphamide. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab) or soluble TNF receptor (e.g., etanercept). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab).

In another example, the other compound is a chemotherapy drug or other drug used for treating cancer.

In another example, the protein described herein is administered before or after radiotherapy for the treatment of cancer.

Dosages and Timing of Administration

Suitable dosages of proteins of the present disclosure will vary depending on the specific protein, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present disclosure comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of protein(s), rather the present disclosure encompasses any amount of the protein(s) sufficient to achieve the stated result in a subject. In one example, a therapeutically effective amount of the protein does not induce neutropenia.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific protein(s) administered and/or the particular subject and/or the type or severity or level of condition and/or predisposition (genetic or otherwise) to the condition. Accordingly, this term is not to be construed to limit the present disclosure to a specific quantity, e.g., weight or amount of protein(s), rather the present disclosure encompasses any amount of the protein(s) sufficient to achieve the stated result in a subject. In one example, a prophylactically effective amount of the protein does not induce neutropenia.

For in vivo administration of the proteins described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, the protein is administered at an initial (or loading) dose of between about 1 mg/kg to about 30 mg/kg, such as from about 1 mg/kg to about 10 mg/kg, or about 1 mg/kg or about 2 mg/kg or 5 mg/kg. The protein can then be administered at a lower maintenance dose of between about 0.01 mg/kg to about 2 mg/kg, such as from about 0.05 mg/kg to about 1 mg/kg, for example, from about 0.1 mg/kg to about 1 mg/kg, such as about 0.1 mg/kg or 0.5 mg/kg or 1 mg/kg. The maintenance doses may be administered every 7-30 days, such as, every 10-15 days, for example, every 10 or 11 or 12 or 13 or 14 or 15 days.

In some examples, the protein is administered at a dose of between about 0.01 mg/kg to about 50 mg/kg, such as between about 0.05 mg/kg to about 30 mg/kg, for example, between about 0.1 mg/kg to about 20 mg/kg, for example, between about 0.1 mg/kg to about 10 mg/kg, such as between about 0.1 mg/kg to about 2 mg/kg. For example, the protein is administered at a dose of between about 0.01 mg/kg to about 5 mg/kg, such as from about 0.1 mg/kg to about 2 mg/kg, such as about 0.2 mg/kg or 0.3 mg/kg or 0.5 mg/kg or 1 mg/kg or 1.5 mg/kg (e.g., without a higher loading dose or a lower maintenance dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the protein is administered every 7 days or every 14 days or every 21 days.

In some examples, at the time of commencing therapy, the mammal is administered the protein on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Administration of a protein according to the methods of the present disclosure can be continuous or intermittent, depending, for example, on the recipient's physiological condition, whether the purpose of the administration is therapeutic or prophylactic, and other factors known to skilled practitioners. The administration of a protein may be essentially continuous over a preselected period of time or may be in a series of spaced doses, e.g., either during or after development of a condition.

NON-LIMITING EXAMPLES

Methods

The Ig and CRH domains of the G-CSFR are involved in ligand binding and receptor dimerization (Layton et al., *J. Biol Chem*, 272: 29735-29741, 1997 and Fukunaga et al, *EMBO J.* 10: 2855-2865 1991). Soluble forms of G-CSFR (with either a C-terminal polyhistidine tag or an Fc sequence) comprising these portions of the receptor have been used in various studies of the receptor, and mutation of the free cysteines at positions 78, 163, and 228 of the receptor assists in expression and isolation of the soluble receptor polypeptide (Mine et al., *Biochem.*, 43: 2458-2464, 2004) without affecting ligand binding. In the present studies soluble forms of the receptor comprising amino acids 25-335 of hG-CSFR with mutations C78A, C163S and C228S were generally used (e.g. SEQ ID NO:1) and the corresponding segment of cynoG-CSFR with the cysteine mutations was generally used for studies on the cynomolgus monkey receptor. Various point mutations of the soluble receptor of SEQ ID NO:1 have also been utilized. Reference to hG-CSFR-Fc means the polypeptide of SEQ ID NO:1 wherein the C-terminal polyhistidine tag has been replaced with an Fc sequence. cynoG-CSFR-Fc means the corresponding segment of cynoG-CSFR with an Fc sequence attached to its C-terminal In some instance the corresponding extracellular domains of the wild type receptor have been used, and in these instances it is specifically noted. The inventors have shown that antibodies and proteins comprising antigen binding sites thereof (e.g., Fab) bind to wild type hG-CSF polypeptides and to these mutant proteins with highly similar affinity. Accordingly, studies using the mutant proteins are a model of studies using wild type hG-CSFR.

Identification of Fabs from Phage Display Library

A phage display library was screened for clones binding to hG-CSFR which eluted upon addition of G-CSF ligand. Fabs were assessed for their ability to bind hG-CSFR, compete G-CSF binding, and cynomolgus G-CSFR cross-reactivity and some clones reformatted as IgG4 antibodies. Potency was then tested through neutralization of G-CSF mediated proliferation in a BaF3 cell line stably transfected with hG-CSFR (described below) and to inhibit CFU-G formation in the presence of G-CSF.

Mammalian Expression Vector Construction for IgG Expression

Mammalian expression vectors were constructed using standard molecular biology techniques by cloning the entire light chain (variable and constant domains) and the variable region of the heavy chain from the selected phage-derived Fab constructs.

Cell Culture and Transient Transfection

Serum-free suspension adapted 293-T cells were obtained from Genechoice Inc. Cells were cultured in FreeStyle™ Expression Medium (Invitrogen) supplemented with penicillin/streptomycin/fungizone reagent (Invitrogen). Prior to transfection the cells were maintained at 37° C. in humidified incubators with an atmosphere of 8% $CO_2$.

The Transient transfection of the mammalian expression vectors using 293-T cells was performed using 293fectin transfection reagent (Invitrogen) according to the manufacturer's instructions. The cell culture supernatants were harvested after 5 days incubation by centrifugation at 2500 rpm and were then passed through a 0.45 µM filter (Nalgene) prior to purification using standard methods for IgG purification.

Control Antibodies

Murine monoclonal antibodies 711, 744 and 774 (Layton et al., Growth Factors, 14: 117-130, 1997) were used as control mouse antibodies.

Affinity Measurements of Fabs

To measure affinity of Fab for G-CSFR or G-CSFR-Fc, Fabs were expressed in E. coli and affinity measured using a Biacore 2000.

Measurement of Binding Kinetics for mAbs

Anti-human (Goat anti-human IgG (gamma) mouse adsorbed, Invitrogen, Cat No. H10500) or anti mouse Fc specific antibody (Jackson Immuno Research Labs inc. Cat No. 515-005-071) was chemically immobilized on a CM-5 sensor surface using amine coupling chemistry.

The immobilized antibodies were then used to capture anti hG-CSFR mAbs from solution. Soluble hG-CSFR proteins (as described in the methods section) were then injected over captured mAb at various concentrations. mAbs were captured for 180 seconds at 0.3 µg/ml. Soluble hG-CSFR at 0, 1.25, 2.5, 5, 10, 20 and 40 nM (in duplicate) was injected for 10 minutes and dissociation was monitored for 30 minutes. Responses from a reference flow cell (in which mAb was not captured, but otherwise treated identically), were subtracted. The responses from a blank injection were then subtracted from the resultant sensorgrams.

The final corrected responses were fitted using non-linear regression to a model describing 1:1 kinetics, including a term for mass transport limitation. The Rmax value was fitted locally, to account for slight deviations in the level of mAb captured. Equilibrium dissociation constant (KD) was determined Kinetic Analysis of Fab C1.2, 5D11, 711 and 744

Fab fragments were generated by papain digestion where 3 mg of antibody was digested (1:500) with pre-activated papain for 40 minutes as per instructions using a papain digestion kit (Sigma, USA). Resultant Fab was purified, by adsorption, away from residual Fc and undigested antibody using protein A purification (mAbSelect, GE, Sweden).

Duplicate biosensor analysis of the Fab were performed using a Biacore 2000 (GE, Sweden) with a doubling dilution of Fab antibodies (100 nM to 0.39 nM in 0.1 mg/ml BSA) at a flow rate of 30 µl/min. Binding (100 µl) was monitored to respective flow cells containing control immobilised blank, immobilized cyno G-CSFR-Fc, immobilized human G-CSFR-Fc and immobilized human G-CSFR. Receptor proteins (20 µg per ml in 20 mM Sodium Acetate pH 4.5) were previously immobilized to a CM5 chip using a NHS/EDC coupling kit as per the manufacturer's instructions (Biacore GE, Sweden). Target immobilization values were set at 700, 700 and 500 resonance units for cyno G-CSFR-Fc, hG-CSFR-Fc and hG-CSFR, respectively. Chip immobilisation was quenched with 50 mM ethanolamine pH 8.0. Dissociation of surface binding was monitored for 1000 seconds prior to desorption of the remaining complex using 50 mM Phosphoric acid. Reference binding was then subtracted from the control channel and kinetics generated using biaevaluation software on the Biacore 2000.

Duplicate biosensor analysis of the antibodies c1.2 and 5D11 in IgG4 format were performed using a Biacore 2000 with a doubling dilution of the antibodies (312 nM to 2.4 nM in 0.1 mg/ml BSA) at a flow rate of 30 ul/min. Binding (100 µl) was monitored to respective flow cells containing control immobilized blank, immobilized cyno-G-CSFR-Fc, immobilized hG-CSFR-Fc and immobilized hG-CSFR. Receptor proteins (20 ug per ml in 20 mM Sodium Acetate pH 4.5) were previously immobilized to a CMS chip using a NHS/EDC coupling kit as per the manufacturer's instructions (Biacore GE, Sweden). Target immobilization values were set at 700, 700 and 500 resonance units for cyno-G-CSFR-Fc, hG-CSFR-Fc and hG-CSFR, respectively. Chip immobilization was quenched with 50 mM ethanolamine pH 8.0. Dissociation of surface binding was monitored for 1000 seconds prior to desorption of the remaining complex using 50 mM Phosphoric acid. Reference binding was then subtracted from the control channel and kinetics generated using biaevaluation software on the Biacore 2000.

BIAcore mAb Kinetics of Affinity Matured C1.2G Antibodies

Anti human (Goat anti Human IgG (gamma) mouse adsorbed, Invitrogen, Cat No. H10500) was chemically immobilised on a CM-5 sensor surface using amine coupling chemistry and then used to capture the C1.2G affinity matured anti hG-CSFR mAbs at 1 mg/ml for 3 mins. Soluble hG-CSFR was then injected over the captured mAb at 0, 10 and 40 nM. Soluble hG-CSFR was injected for 5 minutes and dissociation was monitored for 30 minutes. Responses from a reference flow cell (in which mAb was not captured, but otherwise treated identically), were subtracted. The responses from a blank injection were then subtracted from the resultant sensorgrams.

The final corrected responses were fitted using non-linear regression to a model describing 1:1 kinetics, including a term for mass transport limitation. The Rmax value was fitted locally, to account for slight deviations in the level of mAb captured. Association rate (ka), dissociation rate (kd) and equilibrium dissociation constant ($K_D$) were determined hG-CSFR/BaF3 Proliferation Bioassay—MTT Reduction BaF3 cells expressing hG-CSFR were obtained from the Ludwig Institute Melbourne. To assess the inhibition of G-CSF mediated proliferation by anti hG-CSFR antibodies, serial dilutions of antibody were added to $2 \times 10^4$ cells/well in DME medium with 5% FCS and 0.5 ng/ml hGCSF in 96 well plates and incubated for 48 hours at 37° C., 10% $CO_2$. Cell proliferation was determined by MTT reduction and measured by absorbance at 490 nM.

hG-CSFR/BaF3 Proliferation Bioassay—3H-Thymidine Incorporation

BAF/3 cells engineered to express human G-CSFR and which proliferate in response to human G-CSF were used to measure the ability of various monoclonal antibodies to neutralize the activity of G-CSF. Cells were plated at 1×10⁴ cells in 96 well plates in RPMI/105FCS in the presence of 10 ng/mL human G-CSF and increasing concentrations of various anti-G-CSFR monoclonal antibodies for 48 hours at 37° C. Cells were pulsed with ³H-thymidine for the last 6 hours of culture before being harvested onto glass fibre filters and the level of radioactive thymidine incorporated into DNA determined by liquid scintillation counting.

Human CFU-G Progenitor Bioassay

CD34⁺ bone marrow cells were incubated in semi-solid medium in the presence of 10 ng/ml stem cell factor, 10 ng/ml hG-CSF and titrating concentrations of test antibody. CFU-G were enumerated after 14 days of culture.

Epitope Comparison—Competition Binding

This design of this experiment is built on the premise that for 2 antibodies to be capable of simultaneously binding a single molecule, the epitopes of those 2 antibodies must be different.

Soluble G-CSFR of SEQ ID NO:1 was captured from solution by a surface immobilized antibody. A second antibody was then injected over the complex. Responses from a reference flow cell (in which soluble hG-CSFR was not captured, but otherwise treated identically), were subtracted. Binding of the second antibody indicates that the epitopes of the 2 antibodies differ.

Responses measured at the end of the antibody binding phase were divided by the response at the end of the hG-CSFR capture phase, to correct antibody binding level for the amount of hG-CSFR captured. These capture corrected responses were then used to compare the binding of each antibody to hG-CSFR in the presence of the other antibodies.

Antibodies C1.2, 5D11, 711 and 744 were chemically immobilized on a CM-5 sensor surface using amine coupling chemistry. Soluble hG-CSFR was captured at 100 nM for 180 seconds. Each of the antibodies was then injected in duplicate over captured hG-CSFR at 100 nM for 180 seconds. A blank injection of buffer only was also performed.

Epitope Mapping of C1.2G, 711, 744 and 774

A series of alanine point mutations of SEQ ID NO:1 were generated, expressed in HEK293 cells and then purified. The binding affinity of these mutants for antibodies C1.2, 744 and 774 was measured, and compared to that of SEQ ID NO:1. If a mutation resulted in a change of affinity by more than a factor of 2 from that of SEQ ID NO:1, that residue was deemed to contribute to the binding interaction, and thus is likely to be in or near the epitope. A third mAb (711) with an epitope separate and distinct to C1.2, 744 and 774, was included as a control in order to account for any major structural changes brought about by the mutations.

Anti human (Goat anti Human IgG (gamma) mouse adsorbed, Invitrogen, Cat No. H10500) or anti mouse Fc specific antibody (Jackson Immuno Research Labs inc. Cat No. 515-005-071) was chemically immobilized on a CM-5 sensor surface using amine coupling chemistry. The immobilized antibodies were then used to capture anti hG-CSFR mAbs from solution. Wild-type hG-CSFR ligand binding domain (SEQ ID NO:1) and each alanine point mutant were then injected over captured mAbs at various concentrations. Responses from a reference flow cell (in which mAb was not captured, but otherwise treated identically), were subtracted. The responses from a blank injection were then subtracted from the resultant sensorgrams.

The final corrected responses were fitted using non-linear regression to a model describing 1:1 kinetics, including a term for mass transport limitation. The Rmax value was fitted locally, to account for slight deviations in the level of mAb captured. Association rate (ka), dissociation rate (kd) and equilibrium dissociation constant (KD) were determined C1.2 germline mAb was captured at 0.3 ug/ml for 180 sec, 711 at 1 µg/ml for 180 sec, and 744 and 774 at 5 µg/ml for 180 sec.

For C1.2 and 744 kinetics, WT hG-CSFR and each ala mutant were injected at 0, 2, 10, 50 and 250 nM for 300 sec and dissociation monitored for a further 1800 sec.

For antibody 774 kinetics, WT hG-CSFR and each ala mutant were injected at 0, 2, 10, 50 and 250 nM for 300 sec and dissociation monitored for a further 600 sec.

For antibody 711 kinetics, WT hG-CSFR and each ala mutant were injected at 0 and 100 nM for 180 sec and dissociation monitored for a further 180 sec.

Example 1

Fully Human Anti-hG-CSFR Antibodies are Potent Inhibitors G-CSF Signaling

Using affinity measurements and the BaF3 proliferation assay described above, antibodies 711 and 744 were assessed for affinity to hG-CSFR and G-CSF neutralization assays. Antibody 711 was found to bind to hG-CSFR-Fc fusion (based on SEQ ID NO:1 as discussed in the methods) with an affinity greater than antibody 744 ($K_D$ of 0.86 nM and 8.7 nM, respectively). Using the MTT-based bioassay described above, antibody 711 was also found to more potently inhibit G-CSF-mediated cell proliferation than antibody 744 ($IC_{50}$ (nM G-CSF) of 8.8 nM and 2.4 nM, respectively).

Using the ³H-thymidine incorporation assay, antibody 711 was found to inhibit G-CSF-mediated cell proliferation with an $IC_{50}$ of 10.1 mg/ml; antibody 774 was found to inhibit G-CSF-mediated cell proliferation with an $IC_{50}$ of 37.4 µg/ml and the $IC_{50}$ for antibody 744 was not determinable (see FIG. 1).

Human antibodies isolated from a phage display library (antibodies C1.2 and 5D11) and mouse monoclonal antibody 711 were assessed for their ability to inhibit G-CSF-mediated proliferation of BaF3 cells using the bioassay described above. Results showed that antibody C1.2 inhibited BaF3 proliferation with an $IC_{50}$ of 0.5 nM; antibody 5D11 inhibited proliferation an $IC_{50}$ of 5.9 nM; and 711 inhibited proliferation with an $IC_{50}$ of 3.4 nM.

The antibodies were also assessed for their ability to reduce or inhibit CFU-G formation by CD34⁺ bone marrow cells in the presence of G-CSF as described above. Results showed that antibody C1.2 inhibited CFU-G formation with an $IC_{50}$ of 0.016 nM; antibody 5D11 inhibited CFU-G formation with an $IC_{50}$ of 0.039 nM; and 711 inhibited CFU-G formation with an $IC_{50}$ of 0.411 nM.

Based on these assays, the human antibodies C1.2 and 5D11 are more potent than 711 in inhibiting CFU-G formation and C1.2 is the most potent antibody in both bioassays.

Example 2

Affinity of Antibodies for Human G-CSFR and Cynomolgus Monkey G-CSFR

Affinities of Fabs and IgG4 forms of 5D11 and C1.2 and Fabs of 711 and 744 were also assessed to determine their affinities for the ligand binding domain of hG-CSFR (SEQ ID NO:1), hG-CSFR-Fc and cynomolgus monkey G-CSFR-Fc (based on SEQ ID NO:1 as discussed in the methods). In these assays, the regions of G-CSFR were immobilized and binding of the indicated antibody or fragment to the immobilized polypeptide determined as described in more detail in the general methods (Section entitled "Kinetic analysis of Fab C1.2, 5D11, 711 and 744"). Results are shown in Table 1.

TABLE 1

Affinities of 5D11 and C1.2 for human and cynomolgus monkey G-CSFR

| | Chip Immobilised with: | | |
|---|---|---|---|
| Antibody/Fab | hG-CSFR | hG-CSFR-Fc | cyno G-CSFR-Fc |
| 5D11 Fab | 1.30 nM | 1.20 nM | 0.42 nM |
| C1.2 Fab | 0.37 nM | 0.33 nM | 0.39 nM |
| 5D11 IgG4 | 65 pM | 61 pM | 37 pM |
| C1.2 IgG4 | 27 pM | 77 pM | 54 pM |

These data show that 5D11 and C1.2 have high affinities for hG-CSFR and that these affinities are improved when the Fabs are expressed as complete IgG4 antibodies. Moreover, the affinities for hG-CSFR and cynoG-CSFR for 5D11 or C1.2 are similar. C1.2 has higher affinity for hG-CSFR than 5D11.

The Fab of antibody 711 was shown to have an affinity for hG-CSFR-Fc of 0.86 nM and for cynoG-CSFR of 1.8 µM. The Fab of antibody 744 was shown to have an affinity for hG-CSFR-Fc of 8.7 nM and for cynoG-CSFR of >10 µM. Thus, these Fabs have much poorer affinity for cynoG-CSFR than they do for hG-CSFR.

Reciprocal assays were also performed (i.e., in which antibodies were immobilized and binding of wild type h-GCSFR or wild type cynoG-CSFR to the immobilized antibody was determined in accordance with the general methods (Section entitled "Measurement of Binding Kinetics for mAbs"). Representative results are shown in Table 2.

TABLE 2

Representative affinities of antibodies C1.2G, 5D11, 711, 744 and 774 for wild type hG-CSFR or wild type cynoG-CSFR.

| Captured Antibody | Binding to wt hG-CSFR ($K_D$) | Binding to wt cyno G-CSFR ($K_D$) |
|---|---|---|
| C1.2G (human IgG4) | 1.4 nM | 494 pM |
| 5D11 (human IgG4) | 6.09 nM | 477 pM |
| mAb 711 (mIgG1) | 1.69 nM | 97 nM |
| mAb744 (mIgG2a) | 7.82 nM | Negligible binding |
| mAb774 (mIgG1) | 23.4 nM | Negligible binding |

These data shown that C1.2G and 5D11 bind to wild type cynoG-CSFR with higher affinities than 711, 744 and 774. Moreover, the affinity of C1.2G for wild type hG-CSFR and wild type cynoG-CSFR are within about 3 fold of one another and the affinity of 5D11 for wild type hG-CSFR and wild type cynoG-CSFR are within about 13 fold of one another.

Example 3

Germlining of C1.2

To minimize potential immunogenicity, the variable region framework of C1.2 was changed to match that of the closest human germline framework. This required a single change in the framework of the heavy chain and five changes in the light chain and resulted in a $V_H$ with a sequence set forth in SEQ ID NO: 4 and a $V_L$ with a sequence set forth in SEQ ID NO: 5. Affinity of the germlined antibody (C1.2G) for G-CSFR was similar to C1.2 ($k_a$ 9.54×10$^4$±5.5×10$^3$; $k_d$ 1.31×10$^{-4}$±2.6× 10$^{-6}$; $K_D$ 1.37±0.07 (N=8)). Affinity of C1.2G for hG-CSFR expressed on the cell surface of BaF3 cells was shown to be 257 pM.

Using the $^3$H-thymidine incorporation assay described above, antibody C1.2G was found to inhibit G-CSF-mediated cell proliferation with an IC$_{50}$ of 0.8 µg/ml (FIG. 1).

Reformatting of this antibody into a stabilized IgG4 produced an antibody comprising a heavy chain with a sequence set forth in SEQ ID NO: 64 and a light chain with a sequence set forth in SEQ ID NO: 65.

When expressed in CHO cells a lysine variant of the antibody was observed, i.e., in which one or both of the heavy chains lacked a C-terminal lysine residue (i.e., thus comprising a sequence set forth in SEQ ID NO: 64).

Example 4

Epitope Mapping

Competition Binding

Published data has shown that mAb711 and mAb744 bound to different domains of the hG-CSFR. Competition binding experiments showed that mAb711 but not mAb744 was able to bind to the hG-CSFR subsequent to the binding of C1.2 Ab suggesting that C1.2 binds to a similar region of the receptor as mAb744 but a different region to that of mAb711.

Epitope Excision to Identify Peptides Involved in C1.2 Binding

Epitope excision followed by mass spectrometry analysis was used to identify four peptides of the hG-CSFR that were involved in the binding of C1.2. In this method, the hG-CSFR protein is first bound to an immobilized C1.2 antibody and then digested with proteolytic enzymes. The bound peptides are then identified by MALDI and Electrospray mass spectrometry. The four peptides identified by this approach mapped to positions 111-115, 170-176, 218-234 and/or 286-300 of hG-CSFR (SEQ ID NO: 1).

Binding of C1.2 and mAb744 to hG-CSFR Region Mutants

Figure 2A:
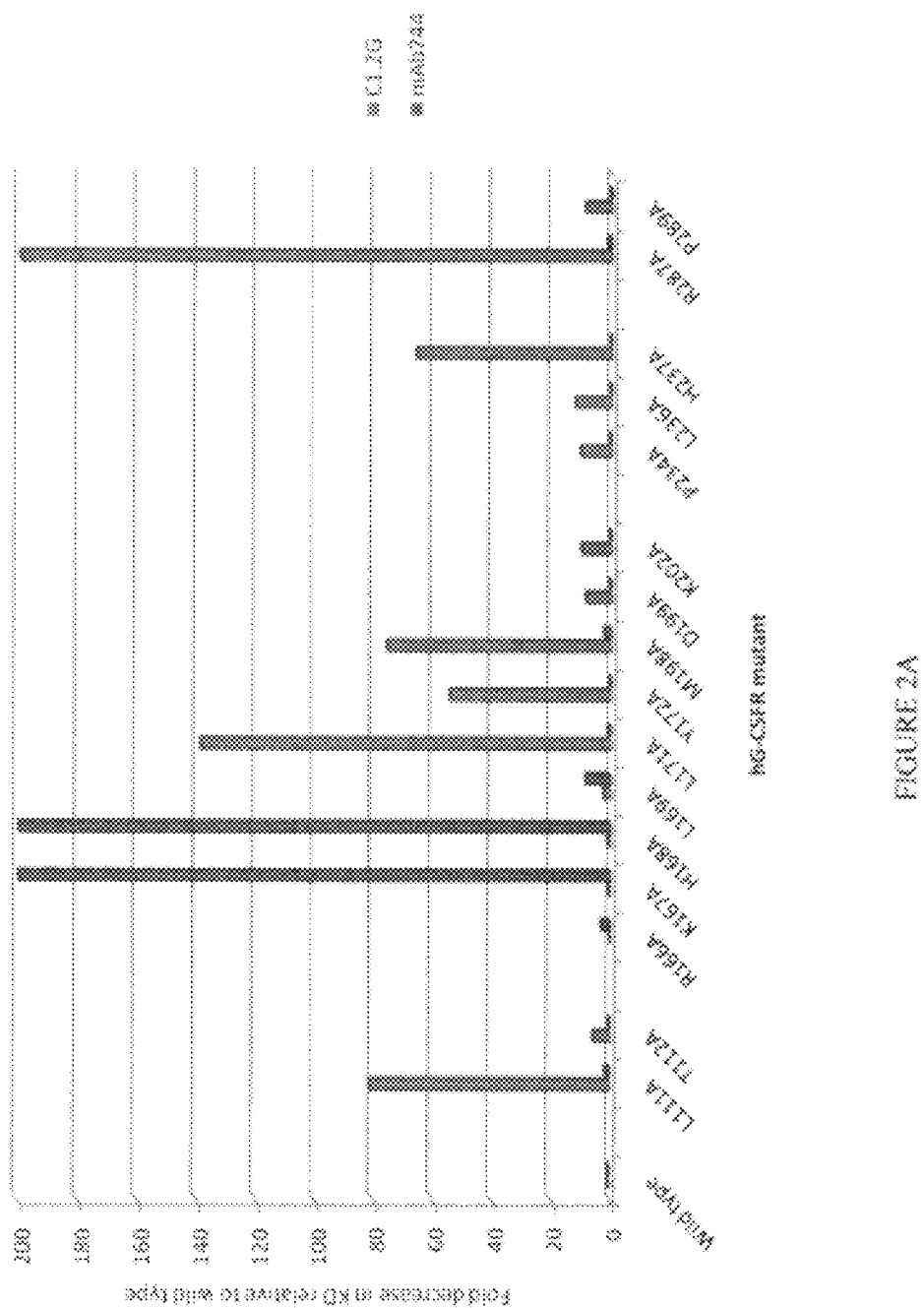
FIG. 2A is a graphical representation showing the relative binding of C1.2G and mAb744 to a series of alanine point mutants of SEQ ID NO: 1 compared to their binding to SEQ ID NO: 1 (positions of mutations are indicated with reference to SEQ ID NO: 1). The fold decrease in $K_D$ of the antibody for the mutant receptor compared to SEQ ID NO: 1 is depicted.

Published data (Tamada et al *Proc Natl Acad Sci USA.* 103:3135-3140, 2006; Aritomi et al *Acta Crystallogr D Biol Crystallogr;* 56:751-753 1999) has identified surface residues on the hG-CSFR. A number of these residues located within the four peptides identified by epitope excision experiments were substituted by alanine and the resulting mutant forms of a region of hG-CSFR were expressed and purified. The binding of C1.2 and mAb744 to each of these mutants was assessed and the key residues involved in binding identified. Results are shown in FIG. 2A. Alanine substitution of residues K167 and H168 resulted in a complete loss of binding by mAb744 whilst binding of C1.2 was unaffected. In contrast, alanine substitution of residue R287 resulted in a complete loss of binding by C1.2 with no effect on mAb744 binding. Other residues that significantly reduced the binding of C1.2 were L111, L171, Y172, M198 and H237. MAb744 bound these mutants at a similar affinity to that of the wild type receptor.

The above assay was repeated with the same antibodies together with mAb774/As shown in FIG. 2B, alanine substitution of residues K167, H168 and L169 resulted in a complete loss of binding by mAb774 whilst binding of C1.2 was unaffected. As with mAb 744, alanine substitution of residue L111, Y172, H237 and R287 had little or no effect on mAb774 binding.

Example 5

Affinity Maturation of C1.2G

Affinity maturation was performed by mutating residues in HCDR3 and/or LCDR3 of C1.2G and screening for Fabs that bound to hG-CSFR. Libraries of mutant antibodies were panned using biotinylated hG-CSFR-Fc recombinant protein, either at a constant concentration over several panning rounds or at reducing concentrations.

At the completion of panning, a number of phage clones were selected from each enriched library and sequenced. Unique clones were then selected based on sequence and reformatted into fully human IgG4/kappa antibodies for binding analysis to hG-CSFR using Biacore (following the general methods in the Section entitled "Measurement of Binding Kinetics for mAbs") and, in some cases ability to inhibit G-CSF-mediated proliferation of BaF3 cells. The reformatted antibodies with improved affinities as compared to the parental C1.2G mAb are listed in Table 3.

TABLE 3

Characteristics of affinity matured antibodies

| mAb | LCDR3 Sequence | HCDR3 Sequence[3] | $K_D$ (M) | IC50 (nM) |
|---|---|---|---|---|
| C1.2G-987 | IQYPQM[1] | LGQSSA | 4.46E-11 | 0.88 |
| C1.2G-95 | WEYPLV[1] | wt | 5.78E-11 | 0.26 |
| C1.2G-79 | QVSWEY[2] | wt | 6.13E-11 | 0.31 |
| C1.2G-83 | WMYALF[1] | wt | 6.60E-11 | 0.21 |
| C1.2G-1003 | WHYPLT[1] | LGSGST | 6.82E-11 | 0.26 |
| C1.2G-44 | YSYPQK[1] | wt | 7.33E-11 | 0.39 |
| C1.2G-97 | FMYPLY[1] | wt | 9.06E-11 | 0.21 |
| C1.2G-986 | YAYPQQ[1] | LGFFQE | 9.11E-11 | 0.28 |
| C1.2G-56 | YMYPIK[1] | wt | 9.93E-11 | 0.22 |
| C1.2G-77 | EQGWNY[2] | wt | 1.07E-10 | 0.23 |
| C1.2G-54 | MWMPMG[1] | LGMFLE | 1.10E-10 | 0.50 |
| C1.2G-802 | HFSMQY[2] | wt | 1.11E-10 | 0.26 |
| C1.2G-967 | WAYGLS[1] | LGMYDL | 1.34E-10 | 0.29 |
| C1.2G-989 | FYYPFY[1] | LGQYMF | 1.44E-10 | 0.34 |
| C1.2G-63 | ANSWGY[2] | wt | 1.61E-10 | 0.26 |
| C1.2G-1002 | WTYGQT[1] | LGMYMN | 1.67E-10 | 0.18 |
| C1.2G-994 | LEYPQM[1] | LGQFMD | 1.70E-10 | 0.49 |
| C1.2G-969 | FQYAQH[1] | LGQYQF | 1.81E-10 | 0.41 |
| C1.2G-1000 | WMYAHM[1] | LGQMMY | 1.82E-10 | 0.34 |

TABLE 3-continued

Characteristics of affinity matured antibodies

| mAb | LCDR3 Sequence | HCDR3 Sequence[3] | $K_D$ (M) | IC50 (nM) |
|---|---|---|---|---|
| C1.2G-94 | WVYPAW[1] | wt | 1.89E-10 | ND |
| C1.2G-975 | WQIKLK[1] | LGQSML | 2.09E-10 | ND |
| C1.2G-75 | EESMNY[2] | wt | 2.11E-10 | ND |
| C1.2G-814 | SQSMEY[2] | wt | 2.21E-10 | ND |
| C1.2G-973 | FKYPMT[1] | LGQMVY | 2.30E-10 | ND |
| C1.2G-977 | WVYHLP[1] | LGEIRE | 2.46E-10 | ND |
| C1.2G-984 | IEYPAH[1] | LGMMQS | 2.50E-10 | ND |
| C1.2G-61 | QQGMWM[2] | wt | 2.57E-10 | ND |
| C1.2G-852 | wt | LGHSLA | 2.92E-10 | ND |
| C1.2G-996 | MWMPIF[1] | LGQYMG | 3.36E-10 | ND |
| C1.2G-43 | IGYPGS[1] | LGQFMR | 3.36E-10 | ND |
| C1.2G-999 | WEYAMF[1] | LGMFHK | 3.56E-10 | ND |
| C1.2G-870 | WMYHKI[1] | wt | 3.67E-10 | ND |
| C1.2G-877 | FRYPFY[1] | wt | 5.08E-10 | ND |
| C1.2G | wt | wt | 6.33E-10 | 0.32 |

[1]Sequence is preceded by the sequence QQS
[2]Sequence is followed by the sequence PLT
[3]Sequence (other than wt) is preceded by the sequence LGE
wt - sequence of CDR3 from C1.2G
ND - not determined Example 6

C1.2G Reduces Neutrophil Levels without Inducing Neutropenia

Figure 3:
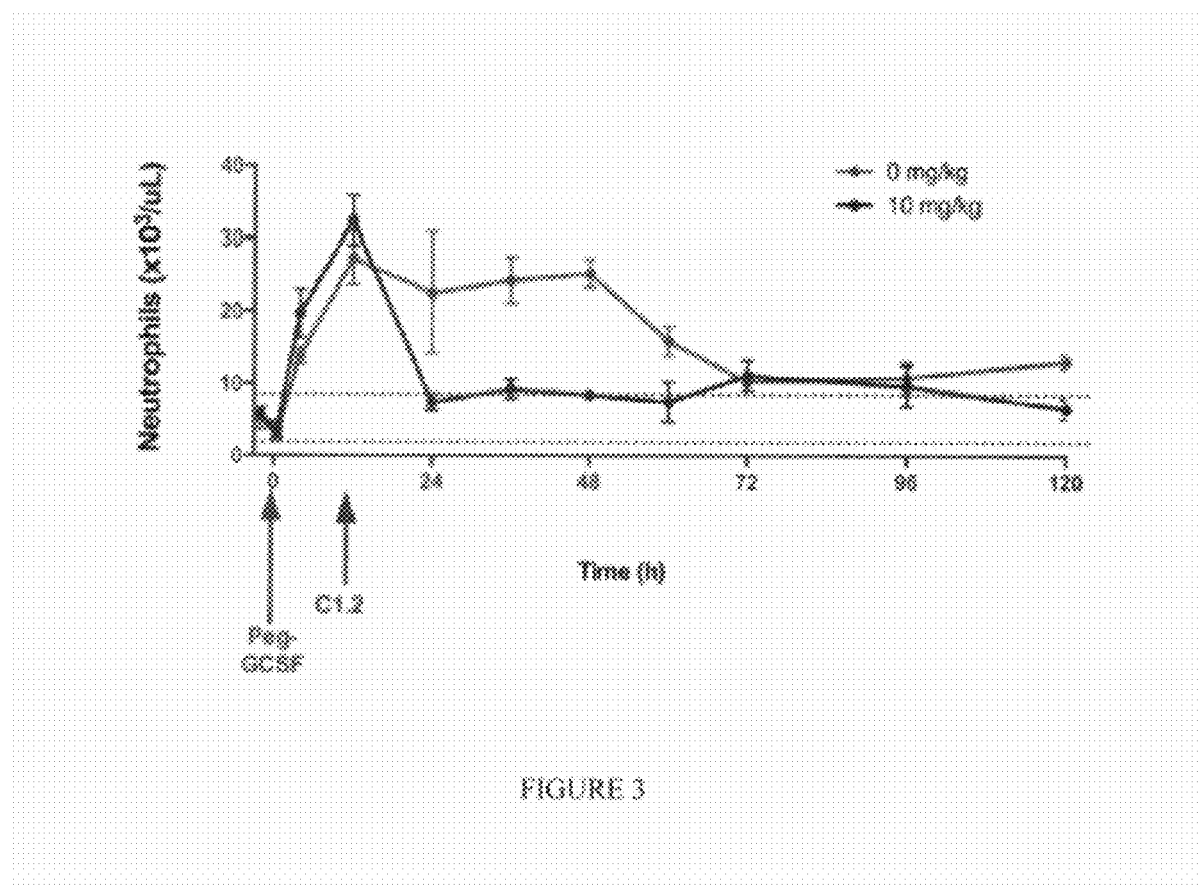
FIG. 3 is a graphical representation showing results of an assay in which pegylated G-CSF was administered to cynomolgus monkeys and one day later C1.2 was administered. The number of neutrophils per μL blood was assessed.

Cynomolgus monkeys were administered pegylated G-CSF and C1.2G (10 mg/kg) administered 12 hours later. As shown in FIG. 3, C1.2 significantly reduced the level of neutrophils compared to control animals, however did not induce neutropenia.

Similar experiments dosing cynomolgus monkeys with between 0.1 to 10 mg/kg of C1.2G 2 hours prior to administration with G-CSF also reduced the level of neutrophils compared to control animals, however did not induce neutropenia.

The invention claimed is:

1. A protein comprising an antigen binding site of an antibody, wherein the antigen binding site of the protein binds to human granulocyte-colony stimulating factor receptor (hG-CSFR) and neutralizes granulocyte-colony stimulating factor (G-CSF) signaling, wherein the protein competitively inhibits the binding of monoclonal antibody C1.2 or monoclonal antibody C1.2 G to one or more of:
  (i) a polypeptide of SEQ ID NO: 1 in which an alanine is substituted for the lysine at position 167 of SEQ ID NO: 1; and/or (ii) a polypeptide of SEQ ID NO: 1 in which an alanine is substituted for the histidine at position 168 of SEQ ID NO: 1, wherein C1.2 comprises a $V_H$ comprising a sequence set forth in SEQ ID NO: 2 and a $V_L$ comprising a sequence set forth in SEQ ID NO: 3, and C1.2 G comprises a $V_H$ comprising a sequence set forth in SEQ ID NO: 4 and a $V_L$ comprising a sequence set forth in SEQ ID NO: 5, wherein the antigen binding site of the protein also binds to the polypeptide at (i) and/or (ii), and wherein the level of binding of the protein to a polypeptide of SEQ ID NO: 1 in which an alanine is substituted for any one of:

(a) the arginine at position 287 of SEQ ID NO:1;

(b) the histidine at position 237 of SEQ ID NO:1;

(c) the methionine at position 198 of SEQ ID NO:1;

(d) the tyrosine at position 172 of SEQ ID NO:1;

(e) the leucine at position 171 of SEQ ID NO:1; or (f) the leucine at position 111 of SEQ ID NO:1 is lower than the level of binding of the protein to a polypeptide of SEQ ID NO: 1 and wherein the protein comprises a $V_H$ and a $V_L$, wherein:

(1) the $V_H$ comprises a CDR1 comprising a sequence set forth in SEQ ID NO: 6, a CDR2 comprising a sequence set forth in SEQ ID NO: 7 and a CDR3 comprising a sequence $LGELGX_1X_2X_3X_4$, wherein:

$X_1$ is selected from the group consisting of tryptophan, glutamine, methionine, serine, phenylalanine, glutamic acid and histidine;

$X_2$ is an amino acid selected from the group consisting of phenylalanine, tyrosine, methionine, serine, glycine and isoleucine;

$X_3$ is an amino acid selected from the group consisting of aspartic acid, methionine, glutamine, serine, leucine, valine, arginine and histidine; and $X_4$ is any amino acid or an amino acid selected from the group consisting of proline, glutamic acid, alanine, leucine, phenylalanine, tyrosine, threonine, asparagine, aspartic acid, serine, glycine, arginine, and lysine; and/or (2) the $V_L$ comprises a CDR1 comprising a sequence set forth in SEQ ID NO: 9, a CDR2 comprising a sequence set forth in SEQ ID NO: 10 and CDR3 comprising a sequence $X_1X_2X_3X_4X_5X_6X_7X_8X_9$, wherein:

$X_1$ is an amino acid selected from the group consisting of glutamine, glutamic acid, histidine, alanine and serine;

$X_2$ is an amino acid selected from the group consisting of glutamine, valine, phenylalanine, asparagine and glutamic acid;

$X_3$ is an amino acid selected from the group consisting of serine and glycine;

$X_4$ is an amino acid selected from the group consisting of tryptophan, methionine, phenylalanine, tyrosine, isoleucine and leucine;

$X_5$ is an amino acid selected from the group consisting of glutamic acid, methionine, glutamine, tryptophan, serine, valine, asparagine, glycine, alanine, arginine, histidine, tyrosine, lysine and threonine;

$X_6$ is an amino acid selected from the group consisting of tyrosine, methionine, isoleucine and threonine;

$X_7$ is an amino acid selected from the group consisting of proline, alanine, histidine, glycine and lysine;

$X_8$ is an amino acid selected from the group consisting of leucine, glutamine, methionine, alanine, phenylalanine, isoleucine, lysine, histidine and glycine; and $X_9$ is an amino acid selected from the group consisting of threonine, phenylalanine, tyrosine, methionine, lysine, serine, histidine, proline, tryptophan, isoleucine, glutamine, glycine and valine.

2. The protein of claim 1, wherein the antigen binding site binds to both human and cynomolgus monkey granulocyte-colony stimulating factor receptor (G-CSFR) with a similar affinity and neutralizes granulocyte-colony stimulating factor (G-CSF) signaling.

3. The protein of claim 1 comprising at least a heavy chain variable region ($V_H$) and a light chain variable region ($V_L$), wherein the $V_H$ and $V_L$ bind to form a Fv comprising an antigen binding domain.

4. The protein of claim 3, wherein the $V_H$ and the $V_L$, are in a single polypeptide chain or wherein the $V_L$ and $V_H$ are in separate polypeptide chains.

5. The protein of claim 4, wherein if the $V_H$ and $V_L$ are in the same polypeptide chain, the protein is:

(i) a single chain Fv fragment (scFv);

(ii) a dimeric scFv (di-scFv); or (iii) at least one of (i) and/or (ii) linked to a constant region of an antibody, a Fc or a heavy chain constant domain ($C_H$) 2 and/or $C_H3$; or if the $V_H$ and $V_L$ are in separate polypeptide chains, the protein is:

(i) a diabody;

(ii) a triabody;

(iii) a tetrabody;

(iv) a Fab;

(v) a $F(ab')_2$;

(vi) a Fv;

(vii) an antibody; or (viii) one of (i) to (vi) linked to a constant region of an antibody, a Fc or a heavy chain constant domain ($C_H$) 2 and/or $C_H3$.

6. The protein of claim 1 which is chimeric, de-immunized, humanized, human or primatized.

7. The protein of claim 1, which inhibits G-CSF-induced proliferation of a BaF3 cell expressing hG-CSFR with an $IC_{50}$ of at least about 0.5 nM.

8. The protein of claim 1, which binds to a polypeptide comprising amino acids 1 to 311 of SEQ ID NO: 1 expressed as a fusion with an antibody Fc region with an affinity of at least about 0.5 nM, wherein affinity is determined in an assay in which the polypeptide is immobilized and the protein or antibody contacts the immobilized polypeptide.

9. The protein of claim 1, which binds to hG-CSFR expressed on the surface of a cell at an affinity of at least about 1 nM.

10. The protein of claim 1 conjugated to another compound.

11. A composition comprising the protein of claim 1 and a pharmaceutically acceptable carrier.

12. A method for treating a granulocyte-colony stimulating factor (G-CSF)-mediated condition in a subject, the method comprising administering the protein of claim 1 to the subject.

13. The method of claim 12 comprising administering an amount of the protein or antibody sufficient to reduce the number of neutrophils in a subject without inducing neutropenia.

14. The method of claim 13, wherein the amount of the protein is between 0.05 mg/kg and 30 mg/kg.

15. The protein of claim 1, which inhibits growth of colony forming units-granulocytes (CFU-G) from CD34+ bone marrow cells grown in the presence of G-CSF with an $IC_{50}$ of 0.2 nM or less.

16. The protein of claim 1, wherein the antigen binding domain binds to an epitope comprising residues within at least one region selected from amino acids 111-115, 170-176, 218-234 and/or 286-300 of SEQ ID NO: 1.

17. The protein of claim 1, wherein upon binding of the protein to a polypeptide of SEQ ID NO: 1 and cleavage using proteolytic enzymes, the protein remains bound to at least one peptide comprising amino acids 111-115 of SEQ ID NO: 1, amino acids 170-176 of SEQ ID NO: 1, amino acids 218-234 of SEQ ID NO: 1, or amino acids 286-300 of SEQ ID NO: 1.

18. The protein of claim 1, the protein comprising a $V_H$ and a $V_L$, wherein:
(i) the $V_H$ comprises:
a complementarity determining region (CDR) 1 comprising the sequence set forth in SEQ ID NO: 6; a CDR2 comprising the sequence set forth in SEQ ID NO: 7; and a CDR3 comprising the sequence set forth in SEQ ID NO: 8, or a CDR3 comprising a sequence having fewer than 5 amino acid substitutions relative to the sequence of SEQ ID NO: 8, or
a sequence set forth in SEQ ID NO: 2, SEQ ID NO: 4, or a sequence having fewer than 5 amino acid substitutions in the framework region relative to the sequence of SEQ ID NO: 2 or SEQ ID NO: 4; and/or
(ii) the $V_L$ comprises:
a CDR1 comprising the sequence set forth in SEQ ID NO: 9; a CDR2 comprising the sequence set forth in SEQ ID NO: 10; and a CDR3 comprising the sequence set forth in SEQ ID NO: 11 or a CDR3 comprising a sequence having fewer than 4 amino acid substitutions relative to the sequence of SEQ ID NO: 11; or
a sequence set forth in SEQ ID NO: 3, SEQ ID NO: 5, or a sequence having fewer than 5 amino acid substitutions in the framework region relative to the sequence of SEQ ID NO: 3 or SEQ ID NO: 5.

19. The protein of claim 1, the protein comprising a $V_H$ and a $V_L$, wherein:
(i) the $V_H$ comprises a CDR1 comprising a sequence set forth in SEQ ID NO: 6, a CDR2 comprising a sequence set forth in SEQ ID NO: 7 and a CDR3 comprising a sequence LGELGX$_1$X$_2$X$_3$X$_4$, wherein:
$X_1$ is selected from the group consisting of tryptophan, glutamine, methionine, serine, phenylalanine, glutamic acid and histidine;
$X_2$ is an amino acid selected from the group consisting of phenylalanine, tyrosine, methionine, serine, glycine and isoleucine;
$X_3$ is an amino acid selected from the group consisting of aspartic acid, methionine, glutamine, serine, leucine, valine, arginine and histidine; and
$X_4$ is any amino acid or an amino acid selected from the group consisting of proline, glutamic acid, alanine, leucine, phenylalanine, tyrosine, threonine, asparagine, aspartic acid, serine, glycine, arginine, and lysine; and
(ii) the $V_L$ comprises a CDR1 comprising a sequence set forth in SEQ ID NO: 9, a CDR2 comprising a sequence set forth in SEQ ID NO: 10 and CDR3 comprising a sequence $X_1X_2X_3X_4X_5X_6X_7X_8X_9$, wherein:
$X_1$ is an amino acid selected from the group consisting of glutamine, glutamic acid, histidine, alanine and serine;
$X_2$ is an amino acid selected from the group consisting of glutamine, valine, phenylalanine, asparagine and glutamic acid;
$X_3$ is an amino acid selected from the group consisting of serine and glycine;
$X_4$ is an amino acid selected from the group consisting of tryptophan, methionine, phenylalanine, tyrosine, isoleucine and leucine;
$X_5$ is an amino acid selected from the group consisting of glutamic acid, methionine, glutamine, tryptophan, serine, valine, asparagine, glycine, alanine, arginine, histidine, tyrosine, lysine and threonine;
$X_6$ is an amino acid selected from the group consisting of tyrosine, methionine, isoleucine and threonine;
$X_7$ is an amino acid selected from the group consisting of proline, alanine, histidine, glycine and lysine;
$X_8$ is an amino acid selected from the group consisting of leucine, glutamine, methionine, alanine, phenylalanine, isoleucine, lysine, histidine and glycine; and
$X_9$ is an amino acid selected from the group consisting of threonine, phenylalanine, tyrosine, methionine, lysine, serine, histidine, proline, tryptophan, isoleucine, glutamine, glycine and valine.

20. The protein of claim 1, the protein comprising a $V_H$ and a $V_L$, wherein:
(i) the $V_H$ comprises:
a complementarity determining region (CDR) 1 comprising the sequence set forth in SEQ ID NO: 6, a CDR2 comprising the sequence set forth in SEQ ID NO: 7 and a CDR3 comprising the sequence set forth in SEQ ID NO: 8; or
a sequence set forth in SEQ ID NO: 2 or SEQ ID NO: 4 and/or
(ii) the $V_L$ comprises:
a CDR1 comprising the sequence set forth in SEQ ID NO: 9, a CDR2 comprising the sequence set forth in SEQ ID NO: 10 and CDR3 comprising the sequence set forth in SEQ ID NO: 11; or
a sequence set forth in SEQ ID NO: 3 or SEQ ID NO: 5.

21. The protein of claim 1, the protein comprising a $V_H$ and a $V_L$, wherein:
(i) the $V_H$ comprises:
a complementarity determining region (CDR) 1 comprising the sequence set forth in SEQ ID NO: 6, a CDR2 comprising the sequence set forth in SEQ ID NO: 7 and a CDR3 comprising the sequence set forth in SEQ ID NO: 8; or a sequence set forth in SEQ ID NO: 2 or SEQ ID NO: 4 and (ii) the $V_L$ comprises:

a CDR1 comprising the sequence set forth in SEQ ID NO: 9, a CDR2 comprising the sequence set forth in SEQ ID NO: 10 and CDR3 comprising the sequence set forth in SEQ ID NO: 11; or a sequence set forth in SEQ ID NO: 3 or SEQ ID NO: 5.

* * * * *

SEQUENCE LISTING

<160> NUMBER OF SEQ ID NOS: 68

<210> SEQ ID NO 1
<211> LENGTH: 319
<212> TYPE: PRT
<213> ORGANISM: artificial
<220> FEATURE:
<223> OTHER INFORMATION: amino acids 25-335 of Homo sapiens G-CSFR
      (hG-CSFR) with a C-terminal polyhistidine tag

<400> SEQUENCE: 1

Glu Cys Gly His Ile Ser Val Ser Ala Pro Ile Val His Leu Gly Asp

```
            1               5                  10                 15
        Pro Ile Thr Ala Ser Cys Ile Ile Lys Gln Asn Cys Ser His Leu Asp
                        20                 25                 30

Pro Glu Pro Gln Ile Leu Trp Arg Leu Gly Ala Glu Leu Gln Pro Gly
                        35                 40                 45

Gly Arg Gln Gln Arg Leu Ser Asp Gly Thr Gln Glu Ser Ile Ile Thr
                50                 55                 60

Leu Pro His Leu Asn His Thr Gln Ala Phe Leu Ser Cys Ala Leu Asn
        65                 70                 75                 80

Trp Gly Asn Ser Leu Gln Ile Leu Asp Gln Val Glu Leu Arg Ala Gly
                        85                 90                 95

Tyr Pro Pro Ala Ile Pro His Asn Leu Ser Cys Leu Met Asn Leu Thr
                        100                105                110

Thr Ser Ser Leu Ile Cys Gln Trp Glu Pro Gly Pro Glu Thr His Leu
                        115                120                125

Pro Thr Ser Phe Thr Leu Lys Ser Phe Lys Ser Arg Gly Asn Cys Gln
                        130                135                140

Thr Gln Gly Asp Ser Ile Leu Asp Cys Val Pro Lys Asp Gly Gln Ser
        145                150                155                160

His Cys Ser Ile Pro Arg Lys His Leu Leu Leu Tyr Gln Asn Met Gly
                        165                170                175

Ile Trp Val Gln Ala Glu Asn Ala Leu Gly Thr Ser Met Ser Pro Gln
                        180                185                190

Leu Cys Leu Asp Pro Met Asp Val Val Lys Leu Glu Pro Pro Met Leu
                        195                200                205

Arg Thr Met Asp Pro Ser Pro Glu Ala Ala Pro Pro Gln Ala Gly Cys
                        210                215                220

Leu Gln Leu Ser Trp Glu Pro Trp Gln Pro Gly Leu His Ile Asn Gln
        225                230                235                240

Lys Cys Glu Leu Arg His Lys Pro Gln Arg Gly Glu Ala Ser Trp Ala
                        245                250                255

Leu Val Gly Pro Leu Pro Leu Glu Ala Leu Gln Tyr Glu Leu Cys Gly
                        260                265                270

Leu Leu Pro Ala Thr Ala Tyr Thr Leu Gln Ile Arg Cys Ile Arg Trp
                        275                280                285

Pro Leu Pro Gly His Trp Ser Asp Trp Ser Pro Ser Leu Glu Leu Arg
                        290                295                300

Thr Thr Glu Arg Ala Pro Thr His His His His His His
        305                310                315

<210> SEQ ID NO 2
        <211> LENGTH: 118
        <212> TYPE: PRT
        <213> ORGANISM: artificial
        <220> FEATURE:
        <223> OTHER INFORMATION: VH of C1.2

<400> SEQUENCE: 2

Glu Val Gln Leu Leu Glu Ser Gly Gly Gly Leu Val Gln Pro Gly Gly
        1               5                  10                 15

Ser Leu Arg Leu Ser Cys Ala Ala Ser Gly Phe Thr Phe Ser Leu Tyr
                        20                 25                 30

Trp Met Gly Trp Val Arg Gln Ala Pro Gly Lys Gly Leu Glu Trp Val
                        35                 40                 45

Ser Ser Ile Ser Ser Ser Gly Gly Val Thr Pro Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Met Leu Gly Glu Leu Gly Trp Phe Asp Pro Trp Gly Gln Gly Thr
                100                 105                 110

Leu Val Thr Val Ser Ser
            115

<210> SEQ ID NO 3
<211> LENGTH: 107
<212> TYPE: PRT
<213> ORGANISM: artificial
<220> FEATURE:
<223> OTHER INFORMATION: VL of C1.2

<400> SEQUENCE: 3

Asp Ile Gln Met Thr Gln Ser Pro Ser Ala Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Ala Ser Asn Leu Gln Asn Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr His Cys Gln Gln Ser Tyr Ser Thr Pro Leu
                 85                  90                  95

Thr Phe Gly Gly Gly Thr Asn Val Glu Ile Arg
                100                 105

<210> SEQ ID NO 4
<211> LENGTH: 118
<212> TYPE: PRT
<213> ORGANISM: artificial
<220> FEATURE:
<223> OTHER INFORMATION: VH of C1.2G

<400> SEQUENCE: 4

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
             20                  25                  30

Trp Met Gly Trp Val Arg Gln Ala Pro Gly Lys Gly Leu Glu Trp Val
         35                  40                  45

Ser Ser Ile Ser Ser Ser Gly Gly Val Thr Pro Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Glu Leu Gly Trp Phe Asp Pro Trp Gly Gln Gly Thr
                100                 105                 110

Leu Val Thr Val Ser Ser
            115
```

```
<210> SEQ ID NO 5
<211> LENGTH: 107
<212> TYPE: PRT
<213> ORGANISM: artificial
<220> FEATURE:
<223> OTHER INFORMATION: VL of C1.2G

<400> SEQUENCE: 5

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 6
<211> LENGTH: 5
<212> TYPE: PRT
<213> ORGANISM: artificial
<220> FEATURE:
<223> OTHER INFORMATION: HCDR1 of C1.2

<400> SEQUENCE: 6

Leu Tyr Trp Met Gly
1               5

<210> SEQ ID NO 7
<211> LENGTH: 17
<212> TYPE: PRT
<213> ORGANISM: artificial
<220> FEATURE:
<223> OTHER INFORMATION: C1.2 HCDR2

<400> SEQUENCE: 7

Ser Ile Ser Ser Ser Gly Gly Val Thr Pro Tyr Ala Asp Ser Val Lys
1               5                   10                  15

Gly

<210> SEQ ID NO 8
<211> LENGTH: 9
<212> TYPE: PRT
<213> ORGANISM: artificial
<220> FEATURE:
<223> OTHER INFORMATION: C1.2 HCDR3

<400> SEQUENCE: 8

Leu Gly Glu Leu Gly Trp Phe Asp Pro
1               5

<210> SEQ ID NO 9
<211> LENGTH: 11
<212> TYPE: PRT
<213> ORGANISM: artificial
<220> FEATURE:
<223> OTHER INFORMATION: C1.2 LCDR1
```

```
<400> SEQUENCE: 9

Arg Ala Ser Gln Gly Ile Ser Ser Tyr Leu Asn
1               5                   10

<210> SEQ ID NO 10
<211> LENGTH: 6
<212> TYPE: PRT
<213> ORGANISM: artificial
<220> FEATURE:
<223> OTHER INFORMATION: C1.2 LCDR2

<400> SEQUENCE: 10

Ala Ser Asn Leu Gln Asn
1               5

<210> SEQ ID NO 11
<211> LENGTH: 9
<212> TYPE: PRT
<213> ORGANISM: artificial
<220> FEATURE:
<223> OTHER INFORMATION: C1.2 LCDR3

<400> SEQUENCE: 11

Gln Gln Ser Tyr Ser Thr Pro Leu Thr
1               5

<210> SEQ ID NO 12
<211> LENGTH: 8
<212> TYPE: PRT
<213> ORGANISM: artificial
<220> FEATURE:
<223> OTHER INFORMATION: consensus sequence of HCDR3 of C1.2
<220> FEATURE:
<221> NAME/KEY: VARIANT
<222> LOCATION: (5)..(5)
<223> OTHER INFORMATION: X is an amino acid selected from the group
      consisting of tryptophan, glutamine, methionine, serine,
      phenylalanine, glutamic acid and histidine
<220> FEATURE:
<221> NAME/KEY: VARIANT
<222> LOCATION: (6)..(6)
<223> OTHER INFORMATION: X is an amino acid selected from the group
      consisting of phenylalanine, tyrosine, methionine, serine, glycine
      and isoleucine
<220> FEATURE:
<221> NAME/KEY: VARIANT
<222> LOCATION: (7)..(7)
<223> OTHER INFORMATION: X is an amino acid selected from the group
      consisting of aspartic acid, methionine, glutamine, serine,
      leucine, valine, arginine and histidine
<220> FEATURE:
<221> NAME/KEY: VARIANT
<222> LOCATION: (8)..(8)
<223> OTHER INFORMATION: X is an amino acid selected from the group
      consisting of proline, glutamic acid, alanine, leucine,
      phenylalanine, tyrosine, threonine, asparagine, aspartic acid,
      serine, glycine, arginine, lysine

<400> SEQUENCE: 12

Leu Gly Glu Leu Xaa Xaa Xaa Xaa
1               5

<210> SEQ ID NO 13
<211> LENGTH: 9
<212> TYPE: PRT
<213> ORGANISM: artificial
<220> FEATURE:
<223> OTHER INFORMATION: consensus sequence of LCDR3 of C1.2
<220> FEATURE:
<221> NAME/KEY: VARIANT
```

```
<222> LOCATION: (1)..(1)
<223> OTHER INFORMATION: X is an amino acid selected from the group
      consisting of glutamine, glutamic acid, histidine, alanine or
      serine
<220> FEATURE:
<221> NAME/KEY: VARIANT
<222> LOCATION: (2)..(2)
<223> OTHER INFORMATION: X is an amino acid selected from the group
      consisting of glutamine, valine, phenylalanine, asparagine and
      glutamic acid
<220> FEATURE:
<221> NAME/KEY: VARIANT
<222> LOCATION: (3)..(3)
<223> OTHER INFORMATION: X is an amino acid selected from the group
      consisting of serine or glycine
<220> FEATURE:
<221> NAME/KEY: VARIANT
<222> LOCATION: (4)..(4)
<223> OTHER INFORMATION: X is an amino acid selected from the group
      consisting of tryptophan, methionine, phenylalanine, tyrosine,
      isoleucine and leucine
<220> FEATURE:
<221> NAME/KEY: VARIANT
<222> LOCATION: (5)..(5)
<223> OTHER INFORMATION: X is an amino acid selected from the group
      consisting of glutamic acid, methionine, glutamine, tryptophan,
      serine, valine, asparagine, glycine, alanine, arginine, histidine,
      tyrosine, lysine or threonine
<220> FEATURE:
<221> NAME/KEY: VARIANT
<222> LOCATION: (6)..(6)
<223> OTHER INFORMATION: X is an amino acid selected from the group
      consisting of tyrosine, methionine, isoleucine or threonine
<220> FEATURE:
<221> NAME/KEY: VARIANT
<222> LOCATION: (7)..(7)
<223> OTHER INFORMATION: X is an amino acid selected from the group
      consisting of proline, alanine, histidine, glycine and lysine
<220> FEATURE:
<221> NAME/KEY: VARIANT
<222> LOCATION: (8)..(8)
<223> OTHER INFORMATION: X is an amino acid selected from the group
      consisting of leucine, glutamine, methionine, alanine,
      phenylalanine, isoleucine, lysine, histidine and glycine
<220> FEATURE:
<221> NAME/KEY: VARIANT
<222> LOCATION: (9)..(9)
<223> OTHER INFORMATION: X is an amino acid selected from the group
      consisting of threonine, phenylalanine, tyrosine, methionine,
      lysine, serine, histidine, proline, tryptophan, isoleucine,
      glutamine, glycine and valine

<400> SEQUENCE: 13

Xaa Xaa Xaa Xaa Xaa Xaa Xaa Xaa Xaa
1               5

<210> SEQ ID NO 14
<211> LENGTH: 107
<212> TYPE: PRT
<213> ORGANISM: artificial
<220> FEATURE:
<223> OTHER INFORMATION: VL of antibody 987

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gln Tyr Pro Gln
                85                  90                  95

Met Phe Gly Gly Gly Thr Lys Val Glu Ile Lys
            100                 105

<210> SEQ ID NO 15
<211> LENGTH: 118
<212> TYPE: PRT
<213> ORGANISM: artificial
<220> FEATURE:
<223> OTHER INFORMATION: VH of antibody 987

<400> SEQUENCE: 15

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Gln Ser Ser Ala Trp Gly Gln Gly Thr
            100                 105                 110

Leu Val Thr Val Ser Ser
        115

<210> SEQ ID NO 16
<211> LENGTH: 107
<212> TYPE: PRT
<213> ORGANISM: artificial
<220> FEATURE:
<223> OTHER INFORMATION: VL of antibody 95

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Glu Tyr Pro Leu
                85                  90                  95

Val Phe Gly Gly Gly Thr Lys Val Glu Ile Lys
            100                 105

<210> SEQ ID NO 17
<211> LENGTH: 107
<212> TYPE: PRT
<213> ORGANISM: artificial

-continued

```
<220> FEATURE:
<223> OTHER INFORMATION: VL of antibody 79

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Val Ser Trp Glu Tyr Pro Leu
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: artificial
<220> FEATURE:
<223> OTHER INFORMATION: VL of antibody 83

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Met Tyr Ala Leu
                85                  90                  95

Phe Phe Gly Gly Gly Thr Lys Val Glu Ile Lys
            100                 105

<210> SEQ ID NO 19
<211> LENGTH: 107
<212> TYPE: PRT
<213> ORGANISM: artificial
<220> FEATURE:
<223> OTHER INFORMATION: VL of antibody 1003

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp His Tyr Pro Leu
                 85                  90                  95

Thr Phe Gly Gly Gly Thr Lys Val Glu Ile Lys
                100                 105

<210> SEQ ID NO 20
<211> LENGTH: 118
<212> TYPE: PRT
<213> ORGANISM: artificial
<220> FEATURE:
<223> OTHER INFORMATION: VH of antibody 1003

<400> SEQUENCE: 20

Glu Val Gln Leu Leu Glu Ser Gly Gly Leu Val Gln Pro Gly Gly
  1               5                  10                  15

Ser Leu Arg Leu Ser Cys Ala Ala Ser Gly Phe Thr Phe Ser Leu Tyr
                 20                  25                  30

Trp Met Gly Trp Val Arg Gln Ala Pro Gly Lys Gly Leu Glu Trp Val
             35                  40                  45

Ser Ser Ile Ser Ser Gly Gly Val Thr Pro Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Glu Leu Gly Ser Gly Ser Thr Trp Gly Gln Gly Thr
                100                 105                 110

Leu Val Thr Val Ser Ser
            115

<210> SEQ ID NO 21
<211> LENGTH: 107
<212> TYPE: PRT
<213> ORGANISM: artificial
<220> FEATURE:
<223> OTHER INFORMATION: VL of antibody 44

<400> SEQUENCE: 21

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
                 20                  25                  30

Leu Asn Trp Tyr Gln Gln Lys Pro Gly Lys Ala Pro Lys Leu Leu Ile
             35                  40                  45

Tyr Tyr Ala Ser Asn Leu Gln Asn Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Tyr Pro Gln
                 85                  90                  95

Lys Phe Gly Gly Gly Thr Lys Val Glu Ile Lys
                100                 105

<210> SEQ ID NO 22
<211> LENGTH: 107
<212> TYPE: PRT
<213> ORGANISM: artificial
```

```
<220> FEATURE:
<223> OTHER INFORMATION: VL of antibody 97

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Met Tyr Pro Leu
                85                  90                  95

Tyr Phe Gly Gly Gly Thr Lys Val Glu Ile Lys
            100                 105

<210> SEQ ID NO 23
<211> LENGTH: 107
<212> TYPE: PRT
<213> ORGANISM: artificial
<220> FEATURE:
<223> OTHER INFORMATION: VL of antibody 986

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ala Tyr Pro Gln
                85                  90                  95

Gln Phe Gly Gly Gly Thr Lys Val Glu Ile Lys
            100                 105

<210> SEQ ID NO 24
<211> LENGTH: 118
<212> TYPE: PRT
<213> ORGANISM: artificial
<220> FEATURE:
<223> OTHER INFORMATION: VH of antibody 986

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Val Thr Pro Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Glu Leu Gly Phe Phe Gln Glu Trp Gly Gln Gly Thr
            100                 105                 110

Leu Val Thr Val Ser Ser
            115

<210> SEQ ID NO 25
<211> LENGTH: 107
<212> TYPE: PRT
<213> ORGANISM: artificial
<220> FEATURE:
<223> OTHER INFORMATION: VL of antibody 56

<400> SEQUENCE: 25

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Tyr
                 20                  25                  30

Leu Asn Trp Tyr Gln Gln Lys Pro Gly Lys Ala Pro Lys Leu Leu Ile
             35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Met Tyr Pro Ile
                 85                  90                  95

Lys Phe Gly Gly Gly Thr Lys Val Glu Ile Lys
            100                 105

<210> SEQ ID NO 26
<211> LENGTH: 107
<212> TYPE: PRT
<213> ORGANISM: artificial
<220> FEATURE:
<223> OTHER INFORMATION: VL of antibody 77

<400> SEQUENCE: 26

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Tyr
                 20                  25                  30

Leu Asn Trp Tyr Gln Gln Lys Pro Gly Lys Ala Pro Lys Leu Leu Ile
             35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Glu Gln Gly Trp Asn Tyr Pro Leu
                 85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: artificial
```

```
<220> FEATURE:
<223> OTHER INFORMATION: VL of antibody 54

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Met Trp Met Pro Met
                85                  90                  95

Gly Phe Gly Gly Gly Thr Lys Val Glu Ile Lys
            100                 105

<210> SEQ ID NO 28
<211> LENGTH: 118
<212> TYPE: PRT
<213> ORGANISM: artificial
<220> FEATURE:
<223> OTHER INFORMATION: VH of antibody 54

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Met Phe Leu Glu Trp Gly Gln Gly Thr
            100                 105                 110

Leu Val Thr Val Ser Ser
        115

<210> SEQ ID NO 29
<211> LENGTH: 107
<212> TYPE: PRT
<213> ORGANISM: artificial
<220> FEATURE:
<223> OTHER INFORMATION: VL of antibody 802

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Phe Ser Met Gln Tyr Pro Leu
                85                  90                  95

Thr Phe Gly Gly Gly Thr Lys Val Glu Ile Lys
            100                 105

<210> SEQ ID NO 30
<211> LENGTH: 107
<212> TYPE: PRT
<213> ORGANISM: artificial
<220> FEATURE:
<223> OTHER INFORMATION: VL of antibody 967

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Ala Tyr Gly Leu
                85                  90                  95

Ser Phe Gly Gly Gly Thr Lys Val Glu Ile Lys
            100                 105

<210> SEQ ID NO 31
<211> LENGTH: 118
<212> TYPE: PRT
<213> ORGANISM: artificial
<220> FEATURE:
<223> OTHER INFORMATION: VH of antibody 967

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Met Tyr Asp Leu Trp Gly Gln Gly Thr
            100                 105                 110

Leu Val Thr Val Ser Ser
        115

<210> SEQ ID NO 32
```

```
<211> LENGTH: 107
<212> TYPE: PRT
<213> ORGANISM: artificial
<220> FEATURE:
<223> OTHER INFORMATION: VL of antibody 989

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Tyr Tyr Pro Phe
                85                  90                  95

Tyr Phe Gly Gly Gly Thr Lys Val Glu Ile Lys
            100                 105

<210> SEQ ID NO 33
<211> LENGTH: 118
<212> TYPE: PRT
<213> ORGANISM: artificial
<220> FEATURE:
<223> OTHER INFORMATION: VH of antibody 989

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Tyr Met Phe Trp Gly Gln Gly Thr
            100                 105                 110

Leu Val Thr Val Ser Ser
        115

<210> SEQ ID NO 34
<211> LENGTH: 107
<212> TYPE: PRT
<213> ORGANISM: artificial
<220> FEATURE:
<223> OTHER INFORMATION: VL of antibody 63

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30
```

-continued

Leu Asn Trp Tyr Gln Gln Lys Pro Gly Lys Ala Pro Lys Leu Leu Ile
             35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Asn Ser Trp Gly Tyr Pro Leu
                 85                  90                  95

Thr Phe Gly Gly Gly Thr Lys Val Glu Ile Lys
             100                 105

<210> SEQ ID NO 35
<211> LENGTH: 107
<212> TYPE: PRT
<213> ORGANISM: artificial
<220> FEATURE:
<223> OTHER INFORMATION: VL of antibody 1002

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Asn Trp Tyr Gln Gln Lys Pro Gly Lys Ala Pro Lys Leu Leu Ile
             35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp Thr Tyr Gly Gln
                 85                  90                  95

Thr Phe Gly Gly Gly Thr Lys Val Glu Ile Lys
             100                 105

<210> SEQ ID NO 36
<211> LENGTH: 118
<212> TYPE: PRT
<213> ORGANISM: artificial
<220> FEATURE:
<223> OTHER INFORMATION: VH of antibody 1002

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
             20                  25                  30

Trp Met Gly Trp Val Arg Gln Ala Pro Gly Lys Gly Leu Glu Trp Val
             35                  40                  45

Ser Ser Ile Ser Ser Ser Gly Gly Val Thr Pro Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Glu Leu Gly Met Tyr Met Asn Trp Gly Gln Gly Thr
             100                 105                 110

Leu Val Thr Val Ser Ser
             115

```
<210> SEQ ID NO 37
<211> LENGTH: 107
<212> TYPE: PRT
<213> ORGANISM: artificial
<220> FEATURE:
<223> OTHER INFORMATION: VL of antibody 994

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Tyr Pro Gln
                85                  90                  95

Met Phe Gly Gly Gly Thr Lys Val Glu Ile Lys
            100                 105

<210> SEQ ID NO 38
<211> LENGTH: 118
<212> TYPE: PRT
<213> ORGANISM: artificial
<220> FEATURE:
<223> OTHER INFORMATION: VH of antibody 994

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Gln Phe Met Asp Trp Gly Gln Gly Thr
            100                 105                 110

Leu Val Thr Val Ser Ser
        115

<210> SEQ ID NO 39
<211> LENGTH: 107
<212> TYPE: PRT
<213> ORGANISM: artificial
<220> FEATURE:
<223> OTHER INFORMATION: VL of antibody 969

<400> SEQUENCE: 39

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Asn Tyr Ala Gln
                85                  90                  95

His Phe Gly Gly Gly Thr Lys Val Glu Ile Lys
            100                 105

<210> SEQ ID NO 40
<211> LENGTH: 118
<212> TYPE: PRT
<213> ORGANISM: artificial
<220> FEATURE:
<223> OTHER INFORMATION: VH of antibody 969

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Gln Tyr Gln Phe Trp Gly Gln Gly Thr
            100                 105                 110

Leu Val Thr Val Ser Ser
        115

<210> SEQ ID NO 41
<211> LENGTH: 107
<212> TYPE: PRT
<213> ORGANISM: artificial
<220> FEATURE:
<223> OTHER INFORMATION: VL of antibody 1000

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Met Tyr Ala His
                85                  90                  95

```
Met Phe Gly Gly Gly Thr Lys Val Glu Ile Lys
            100                 105

<210> SEQ ID NO 42
<211> LENGTH: 118
<212> TYPE: PRT
<213> ORGANISM: artificial
<220> FEATURE:
<223> OTHER INFORMATION: VH of antibody 1000

<400> SEQUENCE: 42

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
            35                  40                  45

Ser Ser Ile Ser Ser Ser Gly Gly Val Thr Pro Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Met Met Tyr Trp Gly Gln Gly Thr
            100                 105                 110

Leu Val Thr Val Ser Ser
        115

<210> SEQ ID NO 43
<211> LENGTH: 107
<212> TYPE: PRT
<213> ORGANISM: artificial
<220> FEATURE:
<223> OTHER INFORMATION: VL of antibody 94

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
            35                  40                  45

Tyr Tyr Ala Ser Asn Leu Gln Asn Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Val Tyr Pro Ala
                85                  90                  95

Trp Phe Gly Gly Gly Thr Lys Val Glu Ile Lys
            100                 105

<210> SEQ ID NO 44
<211> LENGTH: 107
<212> TYPE: PRT
<213> ORGANISM: artificial
<220> FEATURE:
<223> OTHER INFORMATION: VL of antibody 975

<400> SEQUENCE: 44
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Gln Ile Lys Leu
                85                  90                  95

Lys Phe Gly Gly Gly Thr Lys Val Glu Ile Lys
            100                 105
```

<210> SEQ ID NO 45
<211> LENGTH: 118
<212> TYPE: PRT
<213> ORGANISM: artificial
<220> FEATURE:
<223> OTHER INFORMATION: VH of antibody 975

<400> SEQUENCE: 45

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Ser Met Leu Trp Gly Gln Gly Thr
            100                 105                 110

Leu Val Thr Val Ser Ser
        115
```

<210> SEQ ID NO 46
<211> LENGTH: 107
<212> TYPE: PRT
<213> ORGANISM: artificial
<220> FEATURE:
<223> OTHER INFORMATION: VL of antibody 75

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Glu Glu Ser Met Asn Tyr Pro Leu
                85                  90                  95

Thr Phe Gly Gly Gly Thr Lys Val Glu Ile Lys
            100                 105

<210> SEQ ID NO 47
<211> LENGTH: 107
<212> TYPE: PRT
<213> ORGANISM: artificial
<220> FEATURE:
<223> OTHER INFORMATION: VL of antibody 814

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Ala Ser Asn Leu Gln Asn Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ser Gln Ser Met Glu Tyr Pro Leu
                85                  90                  95

Thr Phe Gly Gly Gly Thr Lys Val Glu Ile Lys
            100                 105

<210> SEQ ID NO 48
<211> LENGTH: 107
<212> TYPE: PRT
<213> ORGANISM: artificial
<220> FEATURE:
<223> OTHER INFORMATION: VL of antibody 973

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Ala Ser Asn Leu Gln Asn Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Lys Tyr Pro Met
                85                  90                  95

Thr Phe Gly Gly Gly Thr Lys Val Glu Ile Lys
            100                 105

<210> SEQ ID NO 49
<211> LENGTH: 118
<212> TYPE: PRT
<213> ORGANISM: artificial
<220> FEATURE:
<223> OTHER INFORMATION: VH of antibody 973

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Gln Met Val Tyr Trp Gly Gln Gly Thr
            100                 105                 110

Leu Val Thr Val Ser Ser
            115

<210> SEQ ID NO 50
<211> LENGTH: 107
<212> TYPE: PRT
<213> ORGANISM: artificial
<220> FEATURE:
<223> OTHER INFORMATION: VL of antibody 977

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Val Tyr His Leu
                85                  90                  95

Pro Phe Gly Gly Gly Thr Lys Val Glu Ile Lys
            100                 105

<210> SEQ ID NO 51
<211> LENGTH: 118
<212> TYPE: PRT
<213> ORGANISM: artificial
<220> FEATURE:
<223> OTHER INFORMATION: VH of antibody 977

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Leu Gly Glu Leu Gly Glu Ile Arg Glu Trp Gly Gln Gly Thr
            100                 105                 110

Leu Val Thr Val Ser Ser
        115

<210> SEQ ID NO 52
<211> LENGTH: 107
<212> TYPE: PRT
<213> ORGANISM: artificial
<220> FEATURE:
<223> OTHER INFORMATION: VL of antibody 984

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Glu Tyr Pro Ala
                85                  90                  95

His Phe Gly Gly Gly Thr Lys Val Glu Ile Lys
            100                 105

<210> SEQ ID NO 53
<211> LENGTH: 118
<212> TYPE: PRT
<213> ORGANISM: artificial
<220> FEATURE:
<223> OTHER INFORMATION: VH of antibody 984

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Met Met Gln Ser Trp Gly Gln Gly Thr
            100                 105                 110

Leu Val Thr Val Ser Ser
        115

<210> SEQ ID NO 54
<211> LENGTH: 108
<212> TYPE: PRT
```

```
<213> ORGANISM: artificial
<220> FEATURE:
<223> OTHER INFORMATION: VL of antibody 61

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Met Trp Met Thr Pro
                85                  90                  95

Leu Thr Phe Gly Gly Gly Thr Lys Val Glu Ile Lys
            100                 105

<210> SEQ ID NO 55
<211> LENGTH: 118
<212> TYPE: PRT
<213> ORGANISM: artificial
<220> FEATURE:
<223> OTHER INFORMATION: VH of antibody 852

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly His Ser Leu Ala Trp Gly Gln Gly Thr
            100                 105                 110

Leu Val Thr Val Ser Ser
        115

<210> SEQ ID NO 56
<211> LENGTH: 107
<212> TYPE: PRT
<213> ORGANISM: artificial
<220> FEATURE:
<223> OTHER INFORMATION: VL of antibody 996

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Tyr Ala Ser Asn Leu Gln Asn Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Met Trp Met Pro Ile
                    85                  90                  95

Phe Phe Gly Gly Gly Thr Lys Val Glu Ile Lys
                100                 105

<210> SEQ ID NO 57
<211> LENGTH: 118
<212> TYPE: PRT
<213> ORGANISM: artificial
<220> FEATURE:
<223> OTHER INFORMATION: VH of antibody 996

<400> SEQUENCE: 57

Glu Val Gln Leu Leu Glu Ser Gly Gly Leu Val Gln Pro Gly Gly
  1               5                  10                  15

Ser Leu Arg Leu Ser Cys Ala Ala Ser Gly Phe Thr Phe Ser Leu Tyr
                20                  25                  30

Trp Met Gly Trp Val Arg Gln Ala Pro Gly Lys Gly Leu Glu Trp Val
                35                  40                  45

Ser Ser Ile Ser Ser Ser Gly Val Thr Pro Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Leu Gly Glu Leu Gly Gln Tyr Met Gly Trp Gly Gln Gly Thr
                100                 105                 110

Leu Val Thr Val Ser Ser
            115

<210> SEQ ID NO 58
<211> LENGTH: 107
<212> TYPE: PRT
<213> ORGANISM: artificial
<220> FEATURE:
<223> OTHER INFORMATION: VL of antibody 43

<400> SEQUENCE: 58

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
                35                  40                  45

Tyr Tyr Ala Ser Asn Leu Gln Asn Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ile Gly Tyr Pro Gly
                    85                  90                  95

Ser Phe Gly Gly Gly Thr Lys Val Glu Ile Lys
                100                 105
```

-continued

```
<210> SEQ ID NO 59
<211> LENGTH: 118
<212> TYPE: PRT
<213> ORGANISM: artificial
<220> FEATURE:
<223> OTHER INFORMATION: VH of antibody 43

<400> SEQUENCE: 59
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Gln Phe Met Arg Trp Gly Gln Gly Thr
            100                 105                 110

Leu Val Thr Val Ser Ser
        115

```
<210> SEQ ID NO 60
<211> LENGTH: 107
<212> TYPE: PRT
<213> ORGANISM: artificial
<220> FEATURE:
<223> OTHER INFORMATION: VL of antibody 999

<400> SEQUENCE: 60
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Glu Tyr Ala Met
                85                  90                  95

Phe Phe Gly Gly Gly Thr Lys Val Glu Ile Lys
            100                 105

```
<210> SEQ ID NO 61
<211> LENGTH: 118
<212> TYPE: PRT
<213> ORGANISM: artificial
<220> FEATURE:
<223> OTHER INFORMATION: VH of antibody 999

<400> SEQUENCE: 61
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

```
Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Glu Leu Gly Met Phe His Lys Trp Gly Gln Gly Thr
                100                 105                 110

Leu Val Thr Val Ser Ser
            115

<210> SEQ ID NO 62
<211> LENGTH: 107
<212> TYPE: PRT
<213> ORGANISM: artificial
<220> FEATURE:
<223> OTHER INFORMATION: VL of antibody 870

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
         35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Trp Met Tyr His Lys
                 85                  90                  95

Ile Phe Gly Gly Gly Thr Lys Val Glu Ile Lys
                100                 105

<210> SEQ ID NO 63
<211> LENGTH: 107
<212> TYPE: PRT
<213> ORGANISM: artificial
<220> FEATURE:
<223> OTHER INFORMATION: VL of antibody 877

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
         35                  40                  45

Tyr Tyr Ala Ser Asn Leu Gln Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Arg Tyr Pro Phe
                 85                  90                  95

Tyr Phe Gly Gly Gly Thr Lys Val Glu Ile Lys
```

<210> SEQ ID NO 64
<211> LENGTH: 445
<212> TYPE: PRT
<213> ORGANISM: artificial
<220> FEATURE:
<223> OTHER INFORMATION: C1.2G heavy chain IgG4 with S241P mutation

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
```

-continued

```
                355                 360                 365
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
        435                 440                 445

<210> SEQ ID NO 65
<211> LENGTH: 214
<212> TYPE: PRT
<213> ORGANISM: artificial
<220> FEATURE:
<223> OTHER INFORMATION: C1.2G with kappa light chain

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 836
<212> TYPE: PRT
<213> ORGANISM: Homo sapiens

<400> SEQUENCE: 66

Met Ala Arg Leu Gly Asn Cys Ser Leu Thr Trp Ala Ala Leu Ile Ile
1               5                   10                  15
```

```
Leu Leu Leu Pro Gly Ser Leu Glu Glu Cys Gly His Ile Ser Val Ser
             20                  25                  30

Ala Pro Ile Val His Leu Gly Asp Pro Ile Thr Ala Ser Cys Ile Ile
         35                  40                  45

Lys Gln Asn Cys Ser His Leu Asp Pro Glu Pro Gln Ile Leu Trp Arg
 50                  55                  60

Leu Gly Ala Glu Leu Gln Pro Gly Gly Arg Gln Gln Arg Leu Ser Asp
 65                  70                  75                  80

Gly Thr Gln Glu Ser Ile Ile Thr Leu Pro His Leu Asn His Thr Gln
                 85                  90                  95

Ala Phe Leu Ser Cys Cys Leu Asn Trp Gly Asn Ser Leu Gln Ile Leu
             100                 105                 110

Asp Gln Val Glu Leu Arg Ala Gly Tyr Pro Pro Ala Ile Pro His Asn
         115                 120                 125

Leu Ser Cys Leu Met Asn Leu Thr Thr Ser Ser Leu Ile Cys Gln Trp
130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430
```

```
Thr Arg Leu His Ala Met Ala Arg Asp Pro His Ser Leu Trp Val Gly
        435                 440                 445
Trp Glu Pro Pro Asn Pro Trp Pro Gln Gly Tyr Val Ile Glu Trp Gly
450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
                485                 490                 495
Phe Gln Leu Tyr Glu Ile Ile Val Thr Pro Leu Tyr Gln Asp Thr Met
            500                 505                 510
Gly Pro Ser Gln His Val Tyr Ala Tyr Ser Gln Glu Met Ala Pro Ser
        515                 520                 525
His Ala Pro Glu Leu His Leu Lys His Ile Gly Lys Thr Trp Ala Gln
    530                 535                 540
Leu Glu Trp Val Pro Glu Pro Pro Glu Leu Gly Lys Ser Pro Leu Thr
545                 550                 555                 560
His Tyr Thr Ile Phe Trp Thr Asn Ala Gln Asn Gln Ser Phe Ser Ala
                565                 570                 575
Ile Leu Asn Ala Ser Ser Arg Gly Phe Val Leu His Gly Leu Glu Pro
            580                 585                 590
Ala Ser Leu Tyr His Ile His Leu Met Ala Ala Ser Gln Ala Gly Ala
        595                 600                 605
Thr Asn Ser Thr Val Leu Thr Leu Met Thr Leu Thr Pro Glu Gly Ser
    610                 615                 620
Glu Leu His Ile Ile Leu Gly Leu Phe Gly Leu Leu Leu Leu Leu Thr
625                 630                 635                 640
Cys Leu Cys Gly Thr Ala Trp Leu Cys Cys Ser Pro Asn Arg Lys Asn
                645                 650                 655
Pro Leu Trp Pro Ser Val Pro Asp Pro Ala His Ser Ser Leu Gly Ser
            660                 665                 670
Trp Val Pro Thr Ile Met Glu Glu Asp Ala Phe Gln Leu Pro Gly Leu
        675                 680                 685
Gly Thr Pro Pro Ile Thr Lys Leu Thr Val Leu Glu Glu Asp Glu Lys
    690                 695                 700
Lys Pro Val Pro Trp Glu Ser His Asn Ser Ser Glu Thr Cys Gly Leu
705                 710                 715                 720
Pro Thr Leu Val Gln Thr Tyr Val Leu Gln Gly Asp Pro Arg Ala Val
                725                 730                 735
Ser Thr Gln Pro Gln Ser Gln Ser Gly Thr Ser Asp Gln Val Leu Tyr
            740                 745                 750
Gly Gln Leu Leu Gly Ser Pro Thr Ser Pro Gly Pro Gly His Tyr Leu
        755                 760                 765
Arg Cys Asp Ser Thr Gln Pro Leu Leu Ala Gly Leu Thr Pro Ser Pro
    770                 775                 780
Lys Ser Tyr Glu Asn Leu Trp Phe Gln Ala Ser Pro Leu Gly Thr Leu
785                 790                 795                 800
Val Thr Pro Ala Pro Ser Gln Glu Asp Asp Cys Val Phe Gly Pro Leu
                805                 810                 815
Leu Asn Phe Pro Leu Leu Gln Gly Ile Arg Val His Gly Met Glu Ala
            820                 825                 830
Leu Gly Ser Phe
        835
```

<210> SEQ ID NO 67
<211> LENGTH: 319
<212> TYPE: PRT
<213> ORGANISM: artificial
<220> FEATURE:
<223> OTHER INFORMATION: Ig and CRH domains of Macaca fascicularis
G-CSFR (cynoG-CSFR) with a C-terminal polyhistidine tag

<400> SEQUENCE: 67

```
Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Leu Glu Pro Gln Ile Leu Trp Arg Leu Gly Ala Glu Leu Gln Pro Gly
        35                  40                  45

Gly Arg Gln Gln Arg Leu Ser Asp Gly Ser Gln Gln Ser Thr Ile Thr
    50                  55                  60

Leu Pro His Leu Asn His Thr Arg Ala Phe Leu Ser Cys Ala Leu Asn
65                  70                  75                  80

Trp Gly Asn Ser Leu Gln Ile Leu Asp Gln Val Glu Leu Arg Ala Gly
                85                  90                  95

Tyr Pro Pro Ala Val Pro Arg Asn Leu Ser Cys Leu Met Asn Leu Thr
            100                 105                 110

Thr Ser Ser Leu Ile Cys Gln Trp Glu Pro Gly Pro Glu Thr His Leu
        115                 120                 125

Pro Thr Ser Phe Thr Leu Lys Ser Phe Lys Ser Arg Gly Asn Cys Gln
    130                 135                 140

Thr Gln Gly Asp Ser Ile Met Asp Cys Val Pro Glu Asp Gly Gln Ser
145                 150                 155                 160

His Cys Ser Ile Pro Arg Arg His Leu Leu Leu Tyr Gln Asn Met Gly
                165                 170                 175

Ile Trp Val Gln Ala Glu Asn Ala Leu Gly Thr Ser Met Ser Pro Gln
            180                 185                 190

Leu Cys Leu Glu Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Ser Trp Glu Pro Trp Gln Pro Ala Leu His Ile Asn Gln
225                 230                 235                 240

Lys Cys Glu Leu Arg His Lys Pro Gln Ser Gly Glu Ala Ser Trp Ala
                245                 250                 255

Leu Val Gly Pro Leu Pro Leu Glu Ala Leu Arg Tyr Glu Leu Cys Gly
            260                 265                 270

Leu Leu Pro Ala Thr Ala Tyr Thr Leu Gln Ile Arg Cys Ile Arg Trp
        275                 280                 285

Pro Leu Pro Gly His Trp Ser Asn Trp Ser Pro Ser Leu Glu Leu Arg
    290                 295                 300

Thr Thr Glu Arg Ala Pro Thr His His His His His His His
305                 310                 315
```

<210> SEQ ID NO 68
<211> LENGTH: 444
<212> TYPE: PRT
<213> ORGANISM: artificial
<220> FEATURE:
<223> OTHER INFORMATION: C1.2G heavy chain IgG4 with S241P mutation and
lacking C-terminal lysine residue

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415
```

```
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440
```